(12) United States Patent
Biadatti et al.

(10) Patent No.: US 7,872,026 B2
(45) Date of Patent: Jan. 18, 2011

(54) LIGAND ACTIVATORS OF THE RAR RECEPTORS AND PHARMACEUTICAL/COSMETIC APPLICATIONS THEREOF

(75) Inventors: Thibaud Biadatti, Opio (FR); Olivier Roye, Mouans Sartoux (FR)

(73) Assignee: Galderma Research & Development, Biot (FR)

( * ) Notice: Subject to any disclaimer, the term of this patent is extended or adjusted under 35 U.S.C. 154(b) by 1167 days.

(21) Appl. No.: 11/448,782

(22) Filed: Jun. 8, 2006

(65) Prior Publication Data
US 2007/0021473 A1 Jan. 25, 2007

Related U.S. Application Data

(63) Continuation of application No. PCT/EP2004/014811, filed on Dec. 6, 2004.

(60) Provisional application No. 60/529,762, filed on Dec. 17, 2003.

(30) Foreign Application Priority Data

Dec. 8, 2003 (FR) ................................. 03 14334

(51) Int. Cl.
A61K 31/445 (2006.01)
A61K 31/44 (2006.01)
C07D 213/62 (2006.01)
A61K 31/135 (2006.01)
C07C 62/00 (2006.01)
C07D 307/02 (2006.01)
A61K 31/34 (2006.01)
C07D 333/38 (2006.01)
A61K 31/38 (2006.01)

(52) U.S. Cl. ................. 514/326; 546/298; 514/657; 514/356; 514/461; 514/448; 562/466; 549/484; 549/71

(58) Field of Classification Search .............. 562/466; 514/657, 448, 461, 356; 549/71; 546/298
See application file for complete search history.

(56) References Cited

U.S. PATENT DOCUMENTS 7,148,245 B2 12/2006 Bernardon et al.
2009/0023811 A1* 1/2009 Biadatti et al. .............. 514/569

FOREIGN PATENT DOCUMENTS

EP 0 952 974 B1 11/2001

OTHER PUBLICATIONS

Patani et. al., "Bioisosterism: A Rational Approach in Drug Design", Chem. Rev. 1996, pp. 3147-3176.*
Zcaplus 1999:166584 Abstract, "Biphenyl derivatives substituted by an aromatic or heteroaromatic radical for use in treating keratinization disorders", Bernardon et. al., WO 9910308, Mar. 4, 1999.*
International Search Report PCT/EP2004/014811 dated Mar. 10, 2005.

* cited by examiner

Primary Examiner—Janet L Andres
Assistant Examiner—Binta M Robinson
(74) Attorney, Agent, or Firm—Buchanan Ingersoll & Rooney PC

(57) ABSTRACT
Novel ligand compounds having the structural formula (I):
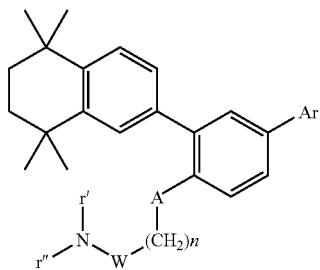
in which:
Ar is a radical selected from among the radical of formulae (a) to (c) below:
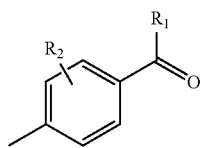
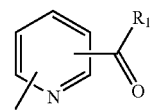
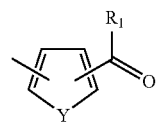
are formulated into pharmaceutical compositions suited for administration in human or veterinary medicine, or, alternatively, into cosmetic compositions.
20 Claims, 1 Drawing Sheet

LIGAND ACTIVATORS OF THE RAR RECEPTORS AND PHARMACEUTICAL/COSMETIC APPLICATIONS THEREOF

CROSS-REFERENCE TO PRIORITY/PCT/PROVISIONAL APPLICATIONS

This application claims priority under 35 U.S.C. §119 of FR 03/14334, filed Dec. 8, 2003, and of Provisional Application No. 60/529,762, filed Dec. 17, 2003, and is a continuation of PCT/EP 2004/014811 filed Dec. 6, 2004 and designating the United States, published in the English language as WO 2005/056516 A1 on Jun. 23, 2005, each hereby expressly incorporated by reference and each assigned to the assignee hereof.

BACKGROUND OF THE INVENTION

1. Technical Field of the Invention

The present invention relates to novel compounds that are useful industrial products, which are ligands that activate RAR receptors. This invention also relates to a process for preparing said novel ligands, and to their formulation into pharmaceutical compositions for administration in human or veterinary medicine, or, alternatively, into cosmetic compositions, and to the non-therapeutic use of these compositions.

2. Description of Background and/or Related and/or Prior Art

Compounds with activity of retinoid type (vitamin A and its derivatives) are widely described in the literature as having activity in cell proliferation and differentiation processes. These properties give this class of compounds high potential in the treatment or prevention of numerous pathologies, and more particularly in dermatology and cancer. Many biological effects of retinoids are mediated by modulating the nuclear retinoic acid receptors (RAR).

The RAR receptors activate transcription by binding to DNA sequence elements, known as RAR response. elements (RARE), in the form of a heterodimer with the retinoid X receptors (known as RXRs).

Three subtypes of human RARs have been identified and described: RARα, RARβ and RARγ.

Chemical compounds with activating activity on receptors of RAR type are known from the prior art. Especially representative are the aromatic heterocyclic biaryl compounds described in EP-0-816,352 B1, which find applications in the treatment of dermatological, rheumatic, respiratory and ophthalmological complaints, conditions or afflictions and also in the cosmetics field.

EP-0-952,974 B1 describes biphenyl derivatives substituted with an aromatic or heteroaromatic radical. When these molecules contain an aminoalkyl on the phenyl ring, they are more difficult to metabolize at this bond.

Thus, need continues to exist for compounds that are metabolized faster in order to limit the residence time of the active agent in the body.

SUMMARY OF THE INVENTION

Novel compounds have now surprisingly and unexpectedly been developed which are ligands that activate retinoic acid receptors, containing a bond that is metabolically cleavable at the phenyl, moiety, permitting satisfaction of this important criterion in the event of administration to humans. These compounds find applications in human medicine, especially in dermatology, and in the cosmetics field.

Thus, the present invention features compounds having the following general formula (I):

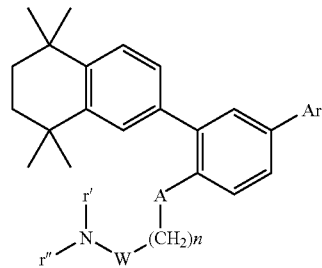

in which:

Ar is a radical selected from among the radicals of formulae (a) to (c) below:

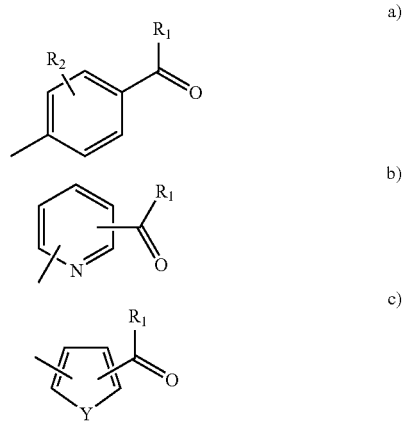

wherein $R_1$ is a radical —$OR_3$ or —$NR_4R_5$ and $R_3$, $R_4$ and $R_5$ are as defined below, wherein $R_2$ is a hydrogen, fluorine or chlorine atom, a methyl radical or a radical $OR_6$ and $R_6$ is as defined below;

$R_3$ is a hydrogen atom, a linear or branched alkyl radical having from 1 to 20 carbon atoms, a mono- or polyhydroxyalkyl radical having from 1 to 20 carbon atoms, a monoaminoalkyl radical having from 1 to 20 carbon atoms, or a sugar residue;

$R_4$ and $R_5$, which may be identical or different, are each a hydrogen atom, a hydroxyl radical, a linear or branched alkyl radical having from 1 to 6 carbon atoms, a mono- or polyhydroxyalkyl radical having from 1 to 20 carbon atoms, or $R_4$ and $R_5$ together form, with the nitrogen atom from which they depend, an amino acid residue or a peptide residue, or, alternatively, $R_4$ and $R_5$ together form with said nitrogen atom a heterocycle;

$R_6$ is a hydrogen atom, a methyl radical or an acetyl radical;

$R_7$ is $CF_3$ or a methyl radical;

r' and r", which may be identical or different, are each a hydrogen atom, a linear, branched or cyclic alkyl radical having from 1 to 4 carbon atoms, or a radical (C=O)$R_7$, or, alternatively, r' and r" with the nitrogen atom from which they depend, together form, a pyrrolidine or piperidine heterocycle;

A is an oxygen atom or a sulfur atom;
n is an integer ranging from 1 and 4;
W is a —CH$_2$— radical;
Y is an oxygen atom or a sulfur atom;

and the salts of the compounds of formula (I) when R$_1$=OH, and also the optical and geometrical isomers of the compounds of formula (I).

When the compounds according to the invention are in the form of a salt, it is preferably a salt of an alkali metal or alkaline-earth metal, or, alternatively, a zinc salt or a salt of an organic amine.

BRIEF DESCRIPTION OF THE DRAWING

The FIGURE of Drawing illustrates certain reaction schemes for preparing the ligand compounds of formula (I).

DETAILED DESCRIPTION OF BEST MODE AND SPECIFIC/PREFERRED EMBODIMENTS OF THE INVENTION

Figure 1:
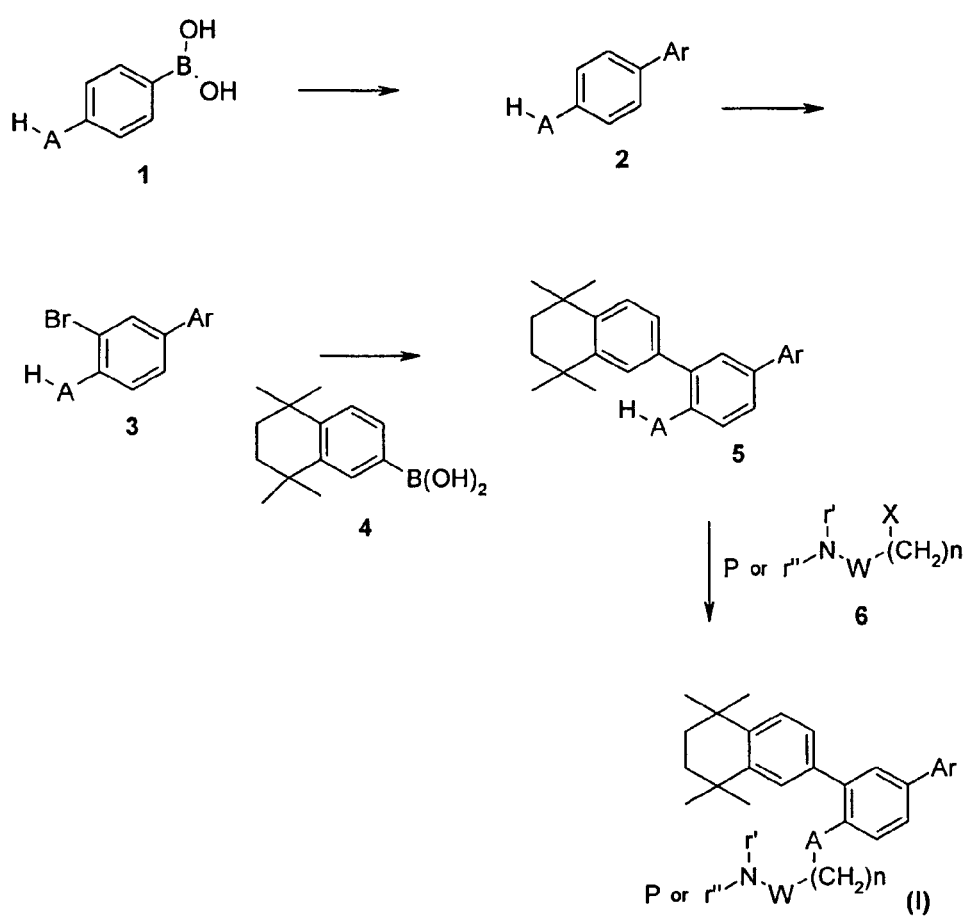

According to the present invention, the term "alkyl having from 1 to 4 carbon atoms" preferably means methyl, ethyl, n-propyl, isopropyl, cyclopropyl, n-butyl, i-butyl or t-butyl radicals.

According to the present invention, the term "alkyl having from 1 to 6 carbon atoms" preferably means methyl, ethyl, n-propyl, isopropyl, cyclopropyl, n-butyl, i-butyl, t-butyl, n-pentyl or n-hexyl radicals.

The term "linear or branched alkyl having from 1 to 20 carbon atoms" especially means methyl, ethyl, propyl, isopropyl, cyclopropyl, n-butyl, i-butyl, t-butyl, n-pentyl, n-hexyl, 2-ethylhexyl, octyl, dodecyl, hexadecyl or octadecyl radicals.

The term "monohydroxyalkyl" means a radical preferably having from 1 to 20 carbon atoms, especially a hydroxymethyl, 2-hydroxyethyl, 2-hydroxypropyl or 3-hydroxypropyl radical.

The term "polyhydroxyalkyl" means a radical preferably having from 3 to 20 carbon atoms and from 2 to 5 hydroxyl groups, such as 2,3-dihydroxypropyl, 2,3,4-trihydroxybutyl or 2,3,4,5-tetrahydroxypentyl radicals or a pentaerythritol residue.

The term "monoaminoalkyl" means a radical preferably having from 1 to 20 carbon atoms and an amino group, especially a 2-aminoethyl, 3-aminopropyl or 4-aminobutyl radical.

The term "sugar residue" means a residue derived especially from glucose, galactose or mannose, or alternatively from glucuronic acid, such as 6'-mannosyl, 6'-glucosyl or 6'-galactosyl.

The term "amino acid residue" especially means a residue derived from lysine, from glycine or from aspartic acid, and the term "peptide residue" more particularly means a dipeptide or tripeptide residue resulting from the combination of amino acids.

According to the present invention, given that W is a —CH$_2$— radical, the general formula (I) may be simplified as follows:

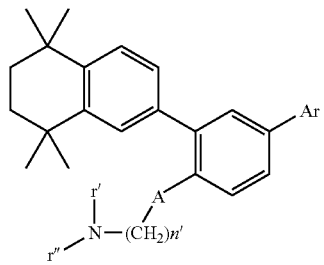

(I)

in which:
Ar, A, r' and r'' are as defined above, and
n' is an integer ranging from 2 to 5.

According to the present invention, the compounds of formula (I) that are more particularly preferred are those for which at least one and preferably all of the conditions below are satisfied:
A is an oxygen atom,
Ar is a radical (a),
R$_1$ is a radical —OR$_3$.

Among the compounds of formula (I) according to the present invention, especially representative are the following:
1. 4'-(4-Isopropylaminobutoxy)-3'-(5,5,8,8-tetramethyl-5,6,7,8-tetrahydronaphth-2-yl)biphenyl-4-carboxylic acid;
2. 4'-(4-Ethylaminobutoxy)-3'-(5,5,8,8-tetramethyl-5,6,7,8-tetrahydronaphth-2-yl)biphenyl-4-carboxylic acid;
3. 4'-(4-Propylaminobutoxy)-3'-(5,5,8,8-tetramethyl-5,6,7,8-tetrahydronaphth-2-yl)biphenyl-4-carboxylic acid;
4. 4'-[4-(Isopropylmethylamino)butoxy]-3'-(5,5,8,8-tetramethyl-5,6,7,8-tetrahydronaphth-2-yl)biphenyl-4-carboxylic acid;
5. 4'-(4-Diethylaminobutoxy)-3'-(5,5,8,8-tetramethyl-5,6,7,8-tetrahydronaphth-2-yl)biphenyl-4-carboxylic acid;
6. 4'-(4-Acetylaminobutoxy)-3'-(5,5,8,8-tetramethyl-5,6,7,8-tetrahydronaphth-2-yl)biphenyl-4-carboxylic acid;
7. 4'-[4-(Acetylethylamino)butoxy]-3'-(5,5,8,8-tetramethyl-5,6,7,8-tetrahydronaphth-2-yl)biphenyl-4-carboxylic acid;
8. 4'-[4-(Acetylisopropylamino)butoxy]-3'-(5,5,8,8-tetramethyl-5,6,7,8-tetrahydronaphth-2-yl)biphenyl-4-carboxylic acid;
9. 4'-(4-Acetylaminobutoxy)-3'-(5,5,8,8-tetramethyl-5,6,7,8-tetrahydronaphth-2-yl)biphenyl-4-carboxylic acid;
10. 4'-(4-Pyrrolidin-1-ylbutoxy)-3'-(5,5,8,8-tetramethyl-5,6,7,8-tetrahydronaphth-2-yl)biphenyl-4-carboxylic acid;
11. 4'-(4-Isopropylaminobutylsulfanyl)-3'-(5,5,8,8-tetramethyl-5,6,7,8-tetrahydronaphth-2-yl)biphenyl-4-carboxylic acid;
12. 4'-(2-Isopropylaminoethoxy)-3'-(5,5,8,8-tetramethyl-5,6,7,8-tetrahydronaphth-2-yl)biphenyl-4-carboxylic acid;
13. 4'-(3-Isopropylaminopropoxy)-3'-(5,5,8,8-tetramethyl-5,6,7,8-tetrahydronaphth-2-yl)biphenyl-4-carboxylic acid;
14. 4'-(5-Isopropylaminopentyloxy)-3'-(5,5,8,8-tetramethyl-5,6,7,8-tetrahydronaphth-2-yl)biphenyl-4-carboxylic acid;
15. 4'-(5-Ethylaminopentyloxy)-3'-(5,5,8,8-tetramethyl-5,6,7,8-tetrahydronaphth-2-yl)biphenyl-4-carboxylic acid;
16. Ethyl 4'-(4-isopropylaminobutoxy)-3'-(5,5,8,8-tetramethyl-5,6,7,8-tetrahydronaphth-2-yl)biphenyl-4-carboxylate;

17. Propyl 4'-(4-isopropylaminobutoxy)-3'-(5,5,8,8-tetramethyl-5,6,7,8-tetrahydronaphth-2-yl)biphenyl-4-carboxylate;
18. Isopropyl 4'-(4-isopropylaminobutoxy)-3'-(5,5,8,8-tetramethyl-5,6,7,8-tetrahydronaphth-2-yl)biphenyl-4-carboxyiate;
19. 2,3-Dihydroxypropyl 4'-(4-isopropylaminobutoxy)-3'-(5,5,8,8-tetramethyl-5,6,7,8-tetrahydronaphth-2-yl)biphenyl-4-carboxylate;
20. 3-Aminopropyl 4'-(4-isopropylaminobutoxy)-3'-(5,5,8,8-tetramethyl-5,6,7,8-tetrahydronaphth-2-yl)biphenyl-4-carboxylate;
21. 6-Glucosyl 4'-(4-isopropylaminobutoxy)-3'-(5,5,8,8-tetramethyl-5,6,7,8-tetrahydronaphth-2-yl)biphenyl-4-carboxylate;
22. 6-Mannosyl 4'-(4-isopropylaminobutoxy)-3'-(5,5,8,8-tetramethyl-5,6,7,8-tetrahydronaphth-2-yl)biphenyl-4-carboxylate;
23. Ethyl 4'-(4-isopropylaminobutoxy)-3'-(5,5,8,8-tetramethyl-5,6,7,8-tetrahydronaphth-2-yl)biphenyl-4-carboxamide;
24. Diethyl 4'-(4-isopropylaminobutoxy)-3'-(5,5,8,8-tetramethyl-5,6,7,8-tetrahydronaphth-2-yl)biphenyl-4-carboxamide;
25. [4'-(4-Isopropylaminobutoxy)-3'-(5,5,8,8-tetramethyl-5,6,7,8-tetrahydronaphth-2-yl)biphenyl-4-yl]pyrrolidin-1-ylmethanone;
26. {[4'-(4-Isopropylaminobutoxy)-3'-(5,5,8,8-tetramethyl-5,6,7,8-tetrahydronaphth-2-yl)biphenyl-4-carbonyl]amino}acetic acid;
27. 3-Hydroxy-2-{[4'-(4-isopropylaminobutoxy)-3'-(5,5,8,8-tetramethyl-5,6,7,8-tetrahydronaphth-2-yl)biphenyl-4-carbonyl]amino}propionic acid;
28. 3-Fluoro-4'-(4-isopropylaminobutoxy)-3'-(5,5,8,8-tetramethyl-5,6,7,8-tetrahydronaphth-2-yl)biphenyl-4-carboxylic acid;
29. 3-Chloro-4'-(4-isopropylaminobutoxy)-3'-(5,5,8,8-tetramethyl-5,6,7,8-tetrahydronaphth-2-yl)biphenyl-4-carboxylic acid;
30. 3-Chloro-4'-(4-isopropylaminobutoxy)-3'-(5,5,8,8-tetramethyl-5,6,7,8-tetrahydronaphth-2-yl)biphenyl-4-carboxylic acid;
31. 3-Hydroxy-4'-(4-isopropylaminobutoxy)-3'-(5,5,8,8-tetramethyl-5,6,7,8-tetrahydronaphth-2-yl)biphenyl-4-carboxylic acid;
32. 4'-(4-Isopropylaminobutoxy)-3-methoxy-3'-(5,5,8,8-tetramethyl-5,6,7,8-tetrahydronaphth-2-yl)biphenyl-4-carboxylic acid;
33. 3-Acetoxy-4'-(4-isopropylaminobutoxy)-3'-(5,5,8,8-tetramethyl-5,6,7,8-tetrahydronaphth-2-yl)biphenyl-4-carboxylic acid;
34. 2-Fluoro-4'-(4-isopropylaminobutoxy)-3'-(5,5,8,8-tetramethyl-5,6,7,8-tetrahydronaphth-2-yl)biphenyl-4-carboxylic acid;
35. 2-Chloro-4'-(4-isopropylaminobutoxy)-3'-(5,5,8,8-tetramethyl-5,6,7,8-tetrahydronaphth-2-yl)biphenyl-4-carboxylic acid;
36. 2-Hydroxy-4'-(4-isopropylaminobutoxy)-3'-(5,5,8,8-tetramethyl-5,6,7,8-tetrahydronaphth-2-yl)biphenyl-4-carboxylic acid;
37. 6-[4-(4-Isopropylaminobutoxy)-3-(5,5,8,8-tetramethyl-5,6,7,8-tetrahydronaphth-2-yl)phenyl]nicotinic acid;
38. 5-[4-(4-Isopropylaminobutoxy)-3-(5,5,8,8-tetramethyl-5,6,7,8-tetrahydronaphth-2-yl)phenyl]pyridine-2-carboxylic acid;
39. 5-[4-(4-Isopropylaminobutoxy)-3-(5,5,8,8-tetramethyl-5,6,7,8-tetrahydronaphth-2-yl)phenyl]thiophene-2-carboxylic acid;
40. 5-[4-(4-Isopropylaminobutoxy)-3-(5,5,8,8-tetramethyl-5,6,7,8-tetrahydronaphth-2-yl)phenyl]furan-2-carboxylic acid;
41. 4-[4-(4-Isopropylaminobutoxy)-3-(5,5,8,8-tetramethyl-5,6,7,8-tetrahydronaphth-2-yl)phenyl]furan-2-carboxylic acid;
42. 4-[4-(4-Isopropylaminobutoxy)-3-(5,5,8,8-tetramethyl-5,6,7,8-tetrahydronaphth-2-yl)phenyl]thiophene-2-carboxylic acid;
43. 5-[4-(4-Isopropylaminobutoxy)-3-(5,5,8,8-tetramethyl-5,6,7,8-tetrahydronaphth-2-yl)phenyl]thiophene-3-carboxylic acid;
44. 5-[4-(4-Isopropylaminobutoxy)-3-(5,5,8,8-tetramethyl-5,6,7,8-tetrahydronaphth-2-yl)phenyl]furan-3-carboxylic acid;
45. 4'-(4-Ethylaminobutoxy)-3-hydroxy-3'-(5,5,8,8-tetramethyl-5,6,7,8-tetrahydronaphth-2-yl)biphenyl-4-carboxylic acid;
46. 3-Hydroxy-4'-(4-propylaminobutoxy)-3'-(5,5,8,8-tetramethyl-5,6,7,8-tetrahydronaphth-2-yl)biphenyl-4-carboxylic acid;
47. 3-Hydroxy-4'-(3-propylaminopropoxy)-3'-(5,5,8,8-tetramethyl-5,6,7,8-tetrahydronaphth-2-yl)biphenyl-4-carboxylic acid;
48. 4'-(4-Piperidin-1-ylbutoxy)-3'-(5,5,8,8-tetramethyl-5,6,7,8-tetrahydronaphth-2-yl)biphenyl-4-carboxylic acid;
49. Ethyl 4'-(3-isopropylaminopropoxy)-3'-(5,5,8,8-tetramethyl-5,6,7,8-tetrahydronaphth-2-yl)biphenyl-4-carboxylate;
50. Ethyl 4'-(3-cyclopropylaminopropoxy)-3'-(5,5,8,8-tetramethyl-5,6,7,8-tetrahydronaphth-2-yl)biphenyl-4-carboxylate;
51. 4'-(3-Cyclopropylaminopropoxy)-3'-(5,5,8,8-tetramethyl-5,6,7,8-tetrahydronaphth-2-yl)biphenyl-4-carboxylic acid;
52. Ethyl 4'-(3-butylaminopropoxy)-3'-(5,5,8,8-tetramethyl-5,6,7,8-tetrahydronaphth-2-yl)biphenyl-4-carboxylate;
53. 4'-(3-Butylaminopropoxy)-3'-(5,5,8,8-tetramethyl-5,6,7,8-tetrahydronaphth-2-yl)biphenyl-4-carboxylic acid;
54. Ethyl 4'-(3-dimethylaminopropoxy)-3'-(5,5,8,8-tetramethyl-5,6,7,8-tetrahydronaphth-2-yl)biphenyl-4-carboxylate;
55. 4'-(3-Dimethylaminopropoxy)-3'-(5,5,8,8-tetramethyl-5,6,7,8-tetrahydronaphth-2-yl)biphenyl-4-carboxylic acid;
56. Ethyl 4'-(3-propylaminopropoxy)-3'-(5,5,8,8-tetramethyl-5,6,7,8-tetrahydronaphth-2-yl)biphenyl-4-carboxylate;
57. 4'-(3-Propylaminopropoxy)-3'-(5,5,8,8-tetramethyl-5,6,7,8-tetrahydronaphth-2-yl)biphenyl-4-carboxylic acid;
58. Ethyl 4'-(4-cyclopropylaminobutoxy)-3'-(5,5,8,8-tetramethyl-5,6,7,8-tetrahydronaphth-2-yl)biphenyl-4-carboxylate;
59. 4'-(4-Cyclopropylaminobutoxy)-3'-(5,5,8,8-tetramethyl-5,6,7,8-tetrahydronaphth-2-yl)biphenyl-4-carboxylic acid;
60. Ethyl 4'-(3-methylaminopropoxy)-3'-(5,5,8,8-tetramethyl-5,6,7,8-tetrahydronaphth-2-yl)biphenyl-4-carboxylate;
61. 4'-(3-Methylaminopropoxy)-3'-(5,5,8,8-tetramethyl-5,6,7,8-tetrahydronaphth-2-yl)biphenyl-4-carboxylic acid;
62. Ethyl 4'-(3-ethylaminopropoxy)-3'-(5,5,8,8-tetramethyl-5,6,7,8-tetrahydronaphth-2-yl)biphenyl-4-carboxylate;
63. 4'-(3-Ethylaminopropoxy)-3'-(5,5,8,8-tetramethyl-5,6,7,8-tetrahydronaphth-2-yl)biphenyl-4-carboxylic acid;

64. Ethyl 4'-(3-aminopropoxy)-3'-(5,5,8,8-tetramethyl-5,6,7,8-tetrahydronaphth-2-yl)biphenyl-4-carboxylate;
65. 4'-(3-Aminopropoxy)-3'-(5,5,8,8-tetramethyl-5,6,7,8-tetrahydronaphth-2-yl)biphenyl-4-carboxylic acid;
66. Ethyl 4'-(2-cyclopropylaminoethoxy)-3'-(5,5,8,8-tetramethyl-5,6,7,8-tetrahydronaphth-2-yl)biphenyl-4-carboxylate;
67. 4'-(2-Cyclopropylaminoethoxy)-3'-(5,5,8,8-tetramethyl-5,6,7,8-tetrahydronaphth-2-yl)biphenyl-4-carboxylic acid;
68. Ethyl 4'-(5-cyclopropylaminopentyloxy)-3'-(5,5,8,8-tetramethyl-5,6,7,8-tetrahydronaphth-2-yl)biphenyl-4-carboxylate;
69. 4'-(5-Cyclopropylaminopentyloxy)-3'-(5,5,8,8-tetramethyl-5,6,7,8-tetrahydronaphth-2-yl)biphenyl-4-carboxylic acid;
70. Ethyl 4'-(2-isopropylaminoethoxy)-3'-(5,5,8,8-tetramethyl-5,6,7,8-tetrahydronaphth-2-yl)biphenyl-4-carboxylate;
71. Ethyl 4'-(5-ethylaminopentyloxy)-3'-(5,5,8,8-tetramethyl-5,6,7,8-tetrahydronaphth-2-yl)biphenyl-4-carboxylate;
72. Ethyl 4'-(5-aminopentyloxy)-3'-(5,5,8,8-tetramethyl-5,6,7,8-tetrahydronaphth-2-yl)biphenyl-4-carboxylate;
73. 4'-(5-Aminopentyloxy)-3'-(5,5,8,8-tetramethyl-5,6,7,8-tetrahydronaphth-2-yl)biphenyl-4-carboxylic acid;
74. Ethyl 4'-(4-aminobutoxy)-3'-(5,5,8,8-tetramethyl-5,6,7,8-tetrahydronaphth-2-yl)biphenyl-4-carboxylate; and
75. 4'-(4-Aminobutoxy)-3'-(5,5,8,8-tetramethyl-5,6,7,8-tetrahydronaphth-2-yl)biphenyl-4-carboxylic acid.

The present invention also features processes for preparing the compounds of formula (I), in particular according to the reaction schemes shown in the FIGURE of Drawing.

The claimed compounds may be obtained from starting materials of formula 1. These boronic acid derivatives may be coupled to corresponding aryl halide derivatives in order to obtain the intermediates of formula 2 under Suzuki coupling conditions. The compounds of formula 3 may then be obtained by bromination, for example in the presence of dibromine, and the precursors 5 may then be obtained after a coupling reaction, for example under the conditions described by Suzuki, of 3 with the boronic acid 4.

Nucleophilic substitution of the phenoxide or thiolate derived from 5 on a compound of type 6, in which X is a leaving group of the tosylate, mesylate, triflate or halide type, makes it possible to obtain the compounds of formula (I). Certain products require a deprotection step at this stage, for example in the case where r' or r" is equal to H (P converted into r' or r"). A product of formula (I) in which r' or r" is equal to H may be subjected to a nucleophilic substitution step or, if applicable, to a reductive amination step to obtain another compound in which r' and r" are other than H.

The compounds according to the invention have activating properties on RAR-type receptors. This RAR-receptor-activating activity is measured in a test of transactivation by means of the dissociation constant Kdapp (apparent).

According to the invention, the expression "activator of RAR-type receptors" means any compound which, for at least one of the RAR subtypes, has a dissociation constant Kdapp of less than or equal to 1 µM, in a transactivation test as described in Example 32.

The preferred compounds of the present invention have, for at least one of the RAR subtypes, a dissociation constant Kdapp of less than or equal to 500 nM and advantageously less than or equal to 100 nM.

The present invention also features the compounds of formula (I) as described above, as medicinal products.

The compounds according to the invention are particularly suitable in the following fields of treatment:

for treating dermatological complaints, conditions or afflictions associated with a keratinization disorder relating to cell differentiation and proliferation, especially for treating common acne, comedones, polymorphs, acne rosacea, nodulocystic acne, acne conglobata, senile acne, and secondary acnes such as solar acne, medication-related acne or occupational acne;

for treating other types of keratinization disorders, especially ichthyosis, ichthyosiform conditions, Darier's disease, palmoplantar keratoderma, leukoplakia and leukoplakiform conditions, and cutaneous or mucous (buccal) lichen;

for treating other dermatological complaints, conditions or afflictions with an inflammatory immunoallergic component, with or without cell proliferation disorder, and especially all forms of psoriasis, whether cutaneous, mucous or ungual, and even psoriatic rheumatism, or cutaneous atopy, such as eczema, or respiratory atopy, or alternatively gingival hypertrophy;

for treating all dermal or epidermal proliferations, whether benign or malignant, and whether of viral origin or otherwise, such as common warts, flat warts and verruciform epidermodysplasia, oral or florid papillomatoses, T lymphoma, and proliferations that may be induced by ultraviolet radiation, especially in the case of basocellular and spinocellular epithelioma, and also any precancerous skin lesion such as keratoacanthomas;

for treating other dermatological disorders such as immune dermatoses, such as lupus erythematosus, immune bullous diseases and collagen diseases, such as scleroderma;

in the treatment of dermatological or general complaints, conditions or afflictions with an immunological component;

for treating certain ophthalmological disorders, especially corneopathies;

for preventing or curing the stigmata of epidermal and/or dermal atrophy induced by local or systemic corticosteroids, or any other form of cutaneous atrophy;

in the treatment of any cutaneous or general complaint, condition or affliction of viral origin;

in the treatment of skin disorders caused by exposure to UV radiation, and also for repairing or combating aging of the skin, whether photoinduced or chronological aging, or for reducing actinic pigmentations and keratosis, or any pathology associated with chronological or actinic aging, such as xerosis;

for combating sebaceous function disorders, such as the hyperseborrhoea of acne or simple seborrhoea;

for preventing or treating cicatrization disorders, or for preventing or repairing stretch marks, or alternatively for promoting cicatrization;

in the treatment of pigmentation disorders, such as hyperpigmentation, melasma, hypopigmentation or vitiligo;

in the treatment of lipid metabolism complaints, conditions or afflictions, such as obesity, hyperlipidaemia, or non-insulin-dependent diabetes;

in the treatment of inflammatory complaints, conditions or afflictions such as arthritis;

in the treatment or prevention of cancerous or precancerous conditions;

in the prevention or treatment of alopecia of various origins, especially alopecia caused by chemotherapy or radiation;

in the treatment of disorders of the immune system, such as asthma, type I sugar diabetes, multiple sclerosis or other selective dysfunctions of the immune system; and in the treatment of complaints, conditions or afflictions of the cardiovascular system, such as arteriosclerosis or hypertension.

This invention also features a pharmaceutical compositions comprising, formulated into a physiologically acceptable medium, at least one compound of formula (I) as defined above.

The present invention also features a novel medicinal compositions suited especially for treating the abovementioned complaints, conditions or afflictions, which comprise, formulated into a pharmaceutically acceptable support that is compatible with the mode of administration selected for this composition, at least one compound of formula (I), an optical isomer or a salt thereof.

The compositions according to the invention may be administered orally, enterally, parenterally, topically or ocularly. The pharmaceutical composition is preferably packaged in a form that is suitable for topical application.

Via the oral route, the composition may be in the form of tablets, gel capsules, dragees, syrups, suspensions, solutions, powders, granules, emulsions, suspensions of microspheres or nanospheres or lipid or polymer vesicles allowing a controlled release. Via the parenteral route, the composition may be in the form of solutions or suspensions for infusion or for injection.

The compounds according to the invention are generally administered in a regime or regimen at a daily dose of about 0.01 mg/kg to 100 mg/kg of body weight, in 1 to 3 dosage intakes.

The compounds are administered systemically, at a concentration generally of from 0.001% to 10% by weight and preferably from 0.01% to 1% by weight, relative to the weight of the composition.

Via the topical route, the pharmaceutical composition according to the invention is more particularly suited for treating the skin and mucous membranes and may be in liquid, pasty or solid form, and more particularly in the form of ointments, creams, milks, pomades, powders, impregnated pads, syndets, solutions, gels, sprays, mousses, suspensions, sticks, shampoos or washing bases. It may also be in the form of suspensions of microspheres or nanospheres or of lipid or polymer vesicles or gelled or polymer patches allowing a controlled release.

The compounds are administered topically at a concentration generally of from 0.001% to 10% by weight and preferably from 0.01% to 1% by weight, relative to the total weight of the composition.

The compounds of formula (I) according to the invention also find application in cosmetics, in particular in body and hair hygiene and especially for treating acne-prone skin, for promoting regrowth of the hair or for limiting hair loss, for combating the greasy appearance of the skin or the hair, in protection against the harmful aspects of sunlight or in the treatment of physiologically dry skin, and for preventing and/or combating photoinduced or chronological aging.

The present invention thus also features compositions comprising, formulated into a cosmetically acceptable support, at least one of the compounds of formula (I).

This invention also features the cosmetic administration of a composition comprising at least one compound of formula (I) for preventing and/or treating the signs of aging and/or dry skin.

This invention also features the cosmetic administration of a composition comprising at least one compound of formula (I) for body or hair hygiene.

The cosmetic compositions according to the invention containing, in a cosmetically acceptable support, at least one compound of formula (I) or an optical or geometrical isomer thereof or a salt thereof, may be especially in the form of a cream, a milk, a gel, suspensions of microspheres or nanospheres or lipid or polymer vesicles, impregnated pads, solutions, sprays, mousses, sticks, soaps, washing bases or shampoos.

The concentration of compound of formula (I) in the cosmetic composition is preferably from 0.001% to 3% by weight, relative to the total weight of the composition.

The term "physiologically acceptable medium" means a medium that is compatible with the skin and optionally with its integuments (eyelashes, nails or hair) and/or mucous membranes.

The pharmaceutical and cosmetic compositions as described above may also contain inert additives, or even pharmacodynamically active additives as regards the pharmaceutical compositions, or combinations of these additives, and especially:

wetting agents;

flavor enhancers;

preservatives such as para-hydroxybenzoic acid esters;

stabilizers;

moisture regulators;

pH regulators;

osmotic pressure modifiers;

emulsifiers;

UV-A and UV-B screening agents;

antioxidants such as α-tocopherol, butylhydroxyanisole, butylhydroxytoluene, superoxide dismutase, ubiquinol or certain metal-chelating agents;

depigmenting agents such as hydroquinone, azelaic acid, caffeic acid or kojic acid;

emollients;

moisturizers, for instance glycerol, PEG 400, thiamorpholinone and its derivatives or urea;

anti-seborrhoeic or anti-acne agents, such as S-carboxymethylcysteine, S-benzylcysteamine, salts thereof or derivatives thereof, or benzoyl peroxide;

antibiotics, for instance erythromycin and its esters, neomycin, clindamycin and its esters, and tetracyclines;

anti-fungal agents such as ketoconazole or poly-4,5-methylene-3-isothiazolidones;

agents for promoting regrowth of the hair, for instance Minoxidil (2,4-diamino-6-piperidinopyrimidine 3-oxide) and its derivatives, Diazoxide (7-chloro-3-methyl-1,2,4-benzothiadiazine 1,1-dioxide) and Phenyloin (5,4-diphenylimidazolidine-2,4-dione);

non-steroidal anti-inflammatory agents;

carotenoids and especially β-carotene;

anti-psoriatic agents such as anthralin and its derivatives;

eicosa-5,8,11,14-tetraynoic acid and eicosa-5,8,11-triynoic acid, and esters and amides thereof;

retinoids, i.e., natural or synthetic RXR receptor ligands;

corticosteroids or oestrogens;

α-hydroxy acids and α-keto acids or derivatives thereof, such as lactic acid, malic acid, citric acid, glycolic acid, mandelic acid, tartaric acid, glyceric acid or ascorbic acid, and also salts, amides or esters thereof, or β-hydroxy acids or derivatives thereof, such as salicylic acid and its salts, amides or esters;

ion-channel blockers such as potassium-channel blockers;

or alternatively, more particularly for pharmaceutical compositions, in combination with medicinal products known to interfere with the immune system (for example cyclosporin, FK 506, glucocorticoids, monoclonal antibodies, cytokines or growth factors, etc.).

Needless to say, one skilled in this art will take care to select the optional compound(s) to be added to these compositions such that the advantageous properties intrinsically associated with the present invention are not, or are not substantially, adversely affected by the envisaged addition.

The present invention also features a cosmetic regime or regimen for enhancing the appearance of the skin, wherein a composition comprising at least one compound of formula (I) as defined above is topically applied onto the skin.

Activation of the retinoic acid receptors with the compounds of formula (I) according to the invention makes it possible to obtain skin of enhanced surface appearance.

Several examples of the production of active compounds of formula (I) according to the invention, biological activity results thereof and also various specific formulations based on such compounds, will now be given, it being understood that same are intended only as illustrative and in nowise limitative. In said examples to follow, all parts and percentages are given by weight, unless otherwise indicated.

EXAMPLE 1

Synthesis of Compound 1

4'-(4-Isopropylaminobutoxy)-3'-(5,5,8,8-tetramethyl-5,6,7,8-tetrahydronaphth-2-yl)biphenyl-4-carboxylic acid a. Preparation of 2,2,2-Trifluoro-N-isopropylacetamide 15 g (260 mmol) of isopropylamine are dissolved in 450 ml of anhydrous THF under an inert atmosphere. 21 ml (260 mmol) of pyridine and 50 mg (cat) of dimethylaminopyridine are added. 40 ml (280 mmol) of trifluoroacetic anhydride are then slowly added dropwise to the reaction medium. The solution is stirred for 15 hours at room temperature and then poured into 500 ml of water and extracted with ethyl acetate. The organic phase is washed with water, dried and concentrated under reduced pressure. A thick oil is obtained, which crystallizes in the form of pink crystals (m=40.5 g, yield=100%).

b. Preparation of N-(4-Bromobutyl)-2,2,2-trifluoro-N-isopropylacetamide 21 g (520 mmol) of 60% sodium hydride are suspended in 700 ml of anhydrous DMF under an inert atmosphere, and the mixture is cooled to 0° C. 40.5 g (260 mmol) of 2,2,2-trifluoro-N-isopropylacetamide are slowly added portionwise. After 15 minutes, 62 ml (520 mmol) of 1,4-dibromobutane are added. The reaction medium is then heated at 60° C. for 3 hours, and then cooled to room temperature, poured into 1 L of water and extracted with ethyl acetate. The organic phase is washed with water and dried, and the residue obtained is purified by distillation. A colorless oil is obtained (m=0.18 g, yield=24%).

c. Preparation of Ethyl 4'-{4-[isopropyl-(2,2,2-trifluoroacetyl)amino]butoxy}-3'-(5,5,8,8-tetramethyl-5,6,7,8-tetrahydronaphth-2-yl)biphenyl-4-carboxylate 1.6 g (39 mmol) of 60% sodium hydride are suspended in 200 ml of anhydrous DMF under an inert atmosphere, and the mixture is cooled to 0° C. 13.9 g (32 mmol) of ethyl 4'-hydroxy-3'-(5,5,8,8-tetramethyl-5,6,7,8-tetrahydronaphth-2-yl)biphenyl-4-carboxylate dissolved in 20 ml of DMF are added slowly. After 20 minutes, 11.3 g (39 mmol) of N-(4-bromobutyl)-2,2,2-trifluoro-N-isopropylacetamide are added. The reaction medium is then heated at 60° C. for 3 hours, and then cooled to room temperature and poured into 500 ml of saturated ammonium chloride solution and extracted with ethyl acetate. The organic phase is washed with water and dried, and the residue obtained is purified by chromatography on a column of silica (eluent: 9/1 heptane/ethyl acetate). A pasty white oil is obtained (m=21.2 g, yield=100%).

d. Synthesis of 4'-(4-Isopropylaminobutoxy)-3'-(5,5,8,8-tetramethyl-5,6,7,8-tetrahydronaphth-2-yl)biphenyl-4-carboxylic acid 1 g (1.5 mmol) of ethyl 4'-{4-[isopropyl-(2,2,2-trifluoroacetyl)amino]butoxy}-3'-(5,5,8,8-tetramethyl-5,6,7,8-tetrahydronaphth-2-yl)biphenyl-4-carboxylate is dissolved in 20 ml of THF. 5 ml of 1 N sodium hydroxide solution are added and the reaction medium is refluxed for 5 hours, and then treated with ammonium chloride solution and extracted with ethyl acetate. The residue obtained is triturated from a heptane/isopropyl ether mixture. A white solid is obtained, m.p.=235° C. (m=520 mg, yield=60%).

$^1$H NMR/DMSO D6: 1.16 (d, J=6.5 Hz, 6H); 1.29 (m, 12H); 1.68 (m, 4H); 1.72 (m, 2H); 1.81 (m, 2H); 2.87 (m, 2H); 3.19 (m, 1H); 4.11 (m, 2H); 7.23 (d, J=8.7 Hz, 1H); 7.35 (m, 2H); 7.57 (d, J=1.25, 1H); 7.32 (d, J=2.4 Hz, 1H); 7.69 (dd, J1=2.4 Hz, J2=8.7 Hz, 1H); 7.81 (d, J=8.4 Hz, 2H); 7.98 (d, J=8.4 Hz, 2H); 8.25 (bs, 1H); 12.8 (bs, 1H).

EXAMPLE 2

Synthesis of Compound 12

4'-(5-isopropylaminoethoxy)-3'-(5,5,8,8-tetramethyl-5,6,7,8-tetrahydronaphth-2-yl)biphenyl-4-carboxylic acid a) Synthesis of 4'-(5-Isopropylaminoethoxy)-3'-(5,5,8,8-tetramethyl-5,6,7,8-tetrahydronaphth-2-yl)biphenyl-4-carboxylic acid By reaction of 200 mg (5 mmol) of sodium hydroxide with 250 mg (0.48 mmol) of ethyl 4'-(5-isopropylaminoethoxy)-3'-(5,5,8,8-tetramethyl-5,6,7,8-tetrahydronaphth-2-yl)biphenyl-4-carboxylate (Example 23a) in 30 ml of tetrahydrofuran, 180 g of 4'-(5-isopropylaminoethoxy)-3'-(5,5,8,8-tetramethyl-5,6,7,8-tetrahydronaphth-2-yl)biphenyl-4-carboxylic acid are obtained in the form of a white solid (m.p.=255° C., yield=76%).

EXAMPLE 3

Synthesis of Compound 13

4'-(3-Isopropylaminopropoxy)-3'-(5,5,8,8-tetramethyl-5,6,7,8-tetrahydronaphth-2-yl)biphenyl-4-carboxylic acid a) Synthesis of 4'-(3-Isopropylaminopropoxy)-3'-(5,5,8,8-tetramethyl-5,6,7,8-tetrahydronaphth-2-yl)biphenyl-4-carboxylic acid 150 mg (3.6 mmol) of sodium hydroxide are added to a solution of 190 mg (0.36 mmol) of ethyl 4'-(3-isopropylaminopropoxy)-3'-(5,5,8,8-tetramethyl-5,6,7,8-tetrahydronaphth-2-yl)biphenyl-4-carboxylate (obtained in Example 1c) in 20 ml of tetrahydrofuran. The reaction mixture is stirred for one day at room temperature and then overnight at reflux. The reaction is stopped by adding water and 1 N hydrochloric acid to pH 5, and then extracted with ethyl acetate. The organic phases are combined and dried over sodium sulfate. The solvents are evaporated off and the residue is then purified by chromatography on silica gel (eluent: 80/20 ethyl acetate/methanol). 60 mg of 4'-(3-isopropylaminopropoxy)-3'-(5,5,8,8-tetramethyl-5,6,7,8-tetrahydronaphth-2-yl)biphenyl-4,4,4,4-carboxylic acid are obtained in the form of a white solid (m.p.=233° C., yield=33%).

EXAMPLE 4

Synthesis of Compound 15

4'-(5-Ethylaminopentyloxy)-3'-(5,5,8,8-tetramethyl-5,6,7,8-tetrahydronaphth-2-yl)biphenyl-4-carboxylic acid a) Synthesis of 4'-(5-Ethylaminopentyloxy)-3'-(5,5,8,8-tetramethyl-5,6,7,8-tetrahydronaphth-2-yl)biphenyl-4-carboxylic acid In a manner similar to that of Example 2a, by reaction of 250 mg (6.25 mmol) of sodium hydroxide with 340 mg (0.63 mmol) of ethyl 4'-(3-ethylaminopentyloxy)-3'-(5,5,8,8-tetramethyl-5,6,7,8-tetrahydronaphth-2-yl)biphenyl-4-carboxylate (Example 21 b) in 30 ml of tetrahydrofuran. 290 mg of 4'-(3-ethylaminopentyloxy)-3'-(5,5,8,8-tetramethyl-5,6,7,8-tetrahydronaphth-2-yl)biphenyl-4-carboxylic acid are obtained in the form of a white solid (m.p.=195° C., yield=90%).

EXAMPLE 5

Synthesis of Compound 49

Ethyl 4'-(3-isopropylaminopropoxy)-3'-(5,5,8,8-tetramethyl-5,6,7,8-tetrahydronaphth-2-yl)biphenyl-4-carboxylate a) Preparation of Ethyl 4'-(3-bromopropoxy)-3'-(5,5,8,8-tetramethyl-5,6,7,8-tetrahydronaphth-2-yl)biphenyl-4-carboxylate 320 µl (3.14 mmol) of 1,3-dibromopropane and 440 mg (3.18 mmol) of potassium carbonate are added to a solution of 900 mg (2.1 mmol, 1 eq) of ethyl 4'-hydroxy-3'-(5,5,8,8-tetramethyl-5,6,7,8-tetrahydronaphth-2-yl)biphenyl-4-carboxylate in 30 ml of methyl ethyl ketone. The reaction mixture is stirred overnight at room temperature and then for 1 day at reflux. The medium is cooled to room temperature and then filtered. The filtrate is evaporated and the residue is purified by chromatography on silica gel (eluent: 90/10 heptane/ethyl acetate). 640 mg of ethyl 4'-(3-bromopropoxy)-3'-(5,5,8,8-tetramethyl-5,6,7,8-tetrahydronaphth-2-yl)biphenyl-4-carboxylate are obtained in the form of a white solid (yield=55%).

b) Preparation of Ethyl 4'-(3-iodopropoxy)-3'-(5,5,8,8-tetramethyl-5,6,7,8-tetrahydronaphth-2-yl)biphenyl-4-carboxylate 260 mg (1.73 mmol) of sodium iodide are added to a solution of 640 mg (1.16 mmol) of ethyl 4'-(3-bromopropoxy)-3'-(5,5,8,8-tetramethyl-5,6,7,8-tetrahydronaphth-2-yl)biphenyl-4-carboxylate in 40 ml of acetone. The reaction mixture is stirred overnight at room temperature. The precipitate formed is filtered off and the filtrate is evaporated. 608 mg of ethyl 4'-(3-iodopropoxy)-3'-(5,5,8,8-tetramethyl-5,6,7,8-tetrahydronaphth-2-yl)biphenyl-4-carboxylate are obtained in the form of a white solid (m.p.=118° C., yield=71%).

c) Synthesis of Ethyl 4-(3-isopropylaminopropoxy)-3'-(5,5,8,8-tetramethyl-5,6,7,8-tetrahydronaphth-2-yl)biphenyl-4-carboxylate 430 µl (5 mmol) of isopropylamine and 420 mg (3 mmol) of potassium carbonate are added to a solution of 600 mg (1 mmol) of ethyl 4'-(3-iodopropoxy)-3'-(5,5,8,8-tetramethyl-5,6,7,8-tetrahydronaphth-2-yl)biphenyl-4-carboxylate in 50 ml of acetonitrile. The reaction mixture is stirred at reflux overnight. The reaction is stopped by adding water and is then extracted with ethyl acetate. The organic phases are combined and dried over sodium sulfate. The solvents are evaporated off and the residue is then purified by chromatography on silica gel (50/50 heptane/ethyl acetate). 160 mg of ethyl 4'-(3-isopropylaminopropoxy)-3'-(5,5,8,8-tetramethyl-5,6,7,8-tetrahydronaphth-2-yl)biphenyl-4-carboxylate are obtained in the form of a yellowish solid (m.p.=171° C., yield=30%).

EXAMPLE 6

Synthesis of Compound 50

Ethyl 4'-(3-cyclopropylaminopropoxy)-3'-(5,5,8,8-tetramethyl-5,6,7,8-tetrahydronaphth-2-yl)biphenyl-4-carboxylate a) Synthesis of Ethyl 4'-(3-cyclopropylaminopropoxy)-3'-(5,5,8,8-tetramethyl-5,6,7,8-tetrahydronaphth-2-yl)biphenyl-4-carboxylate In a manner similar to that of Example 1c, by reaction of 1.7 ml (24.5 mmol) of cyclopropylamine with 670 mg (1.12 mmol) of ethyl 4'-(3-iodopropoxy)-3'-(5,5,8,8-tetramethyl-5,6,7,8-tetrahydronaphth-2-yl)biphenyl-4-carboxylate (obtained in Example 1b) in 50 ml of ethanol. 350 mg of ethyl 4'-(3-cyclopropylaminopropoxy)-3'-(5,5,8,8-tetramethyl-5,6,7,8-tetrahydronaphth-2-yl)biphenyl-4-carboxylate are obtained in the form of a white solid (m.p.=141° C., yield=59%).

EXAMPLE 7

Synthesis of Compound 51

4'-(3-Cyclopropylaminopropoxy)-3'-(5,5,8,8-tetramethyl-5,6,7,8-tetrahydronaphth-2-yl)biphenyl-4-carboxylic acid a) Synthesis of 4'-(3-Cyclopropylaminopropoxy)-3'-(5,5,8,8-tetramethyl-5,6,7,8-tetrahydronaphth-2-yl)biphenyl-4-carboxylic acid In a manner similar to that of Example 2a, by reaction of 260 mg (6.5 mmol) of sodium hydroxide with 340 mg (0.65 mmol) of ethyl 4'-(3-cyclopropylaminopropoxy)-3'-(5,5,8,8-tetramethyl-5,6,7,8-tetrahydronaphth-2-yl)biphenyl-4-carboxylate (Example 3a) in 30 ml of tetrahydrofuran. 160 mg of 4'-(3-cyclopropylaminopropoxy)-3'-(5,5,8,8-tetramethyl-5,6,7,8-tetrahydronaphth-2-yl)biphenyl-4-carboxylic acid are obtained in the form of a white solid (m.p.=192° C., yield=50%).

EXAMPLE 8

Synthesis of Compound 52

Ethyl 4'-(3-butylaminopropoxy)-3'-(5,5,8,8-tetramethyl-5,6,7,8-tetrahydronaphth-2-yl)biphenyl-4-carboxylate a) Synthesis of Ethyl 4'-(3-butylaminopropoxy)-3'-(5,5,8,8-tetramethyl-5,6,7,8-tetrahydronaphth-2-yl)biphenyl-4-carboxylate In a manner similar to that of Example 1c, by reaction of 1.9 ml (19.3 mmol) of n-butylamine and 750 mg (1.29 mmol) of ethyl 4'-(3-iodopropoxy)-3'-(5,5,8,8-tetramethyl-5,6,7,8-tetrahydronaphth-2-yl)biphenyl-4-carboxylate (obtained in Example 1b) in 50 ml of ethanol. 380 mg of ethyl 4'-(3-butylaminopropoxy)-3'-(5,5,8,8-tetramethyl-5,6,7,8-tetrahydronaphth-2-yl)biphenyl-4-carboxylate are obtained in the form of a white solid (m.p.=175° C., yield=59%).

EXAMPLE 9

Synthesis of Compound 53

4'-(3-Butylaminopropoxy)-3'-(5,5,8,8-tetramethyl-5,6,7,8-tetrahydronaphth-2-yl)biphenyl-4-carboxylic acid a) Synthesis of 4'-(3-Butylaminopropoxy)-3'-(5,5,8,8-tetramethyl-5,6,7,8-tetrahydronaphth-2-yl)biphenyl-4-carboxylic acid In a manner similar to that of Example 2a, by reaction of 410 mg (10 mmol) of sodium hydroxide with 360 mg (0.7 mmol) of ethyl 4'-(3-butylaminopropoxy)-3'-(5,5,8,8-tetramethyl-5,6,7,8-tetrahydronaphth-2-yl)biphenyl-4-carboxylate (Example 5a) in 30 ml of tetrahydrofuran. 70 mg of 4'-(3-butylaminopropoxy)-3'-(5,5,8,8-tetramethyl-5,6,7,8-tetrahydronaphth-2-yl)biphenyl-4-carboxylic acid are obtained in the form of a white solid (m.p.=238° C., yield=20%).

EXAMPLE 10

Synthesis of Compound 54

Ethyl 4'-(3-dimethylaminopropoxy)-3'-(5,5,8,8-tetramethyl-5,6,7,8-tetrahydronaphth-2-yl)biphenyl-4-carboxylate a) Synthesis of Ethyl 4'-(3-dimethylaminopropoxy)-3'-(5,5,8,8-tetramethyl-5,6,7,8-tetrahydronaphth-2-yl)biphenyl-4-carboxylate 440 mg (2.78 mmol) of 3-dimethylaminopropyl chloride hydrochloride and 970 mg (7 mmol) of potassium carbonate are added to a solution of 1 g (2.33 mmol) of ethyl 4'-hydroxy-3'-(5,5,8,8-tetramethyl-5,6,7,8-tetrahydronaphth-2-yl)biphenyl-4-carboxylate in 50 ml of acetone. The reaction mixture is stirred for 48 hours at reflux. The reaction is stopped by adding water, and is then extracted with ethyl acetate. The organic phases are combined and dried over sodium sulfate. The solvents are evaporated off and the residue is then purified by chromatography on silica gel (eluent: 90/10 ethyl acetate/methanol). 980 mg of ethyl 4'-(3-dimethylaminopropoxy)-3'-(5,5,8,8-tetramethyl-5,6,7,8-tetrahydronaphth-2-yl)biphenyl-4-carboxylate are obtained in the form of a yellow oil (yield=82%).

$^1$H NMR (CDCl$_3$, 400 MHz): 1.30 (s, 12H); 1.44 (t, J=7.1, 3H); 1.75 (s, 4H); 1.96 (m, 2H); 2.22 (s, 6H); 2.40 (t, J=7 Hz, 2H); 4.10 (t, J=7.2 Hz, 2H); 4.42 (q, J=7.2 Hz, 2H); 7.09 (d, J=8.5 Hz, 1H); 7.36-7.38 (m, 2H); 7.55-7.58 (m, 2H); 7.63-7.69 (m, 2H); 8.10-8.12 (m, 2H).

EXAMPLE 11

Synthesis of Compound 55

4'-(3-Dimethylaminopropoxy)-3'-(5,5,8,8-tetramethyl-5,6,7,8-tetrahydronaphth-2-yl)biphenyl-4-carboxylic acid a) Synthesis of 4'-(3-Dimethylaminopropoxy)-3'-(5,5,8,8-tetramethyl-5,6,7,8-tetrahydronaphth-2-yl)biphenyl-4-carboxylic acid In a manner similar to that of Example 2a, by reaction of 1.12 g (28 mmol) of sodium hydroxide with 960 mg (1.87 mmol) of ethyl 4'-(3-dimethylaminopropoxy)-3'-(5,5,8,8-tetramethyl-5,6,7,8-tetrahydronaphth-2-yl)biphenyl-4-carboxylate (Example 7a) in 30 ml of tetrahydrofuran. 820 mg of 4'-(3-dimethylaminopropoxy)-3'-(5,5,8,8-tetramethyl-5,6,7,8-tetrahydronaphth-2-yl)biphenyl-4-carboxylic acid are obtained in the form of a white solid (m.p.=199° C., yield=90%).

EXAMPLE 12

Synthesis of Compound 56

Ethyl 4'-(3-propylaminopropoxy)-3'-(5,5,8,8-tetramethyl-5,6,7,8-tetrahydronaphth-2-yl)biphenyl-4-carboxylate a) Synthesis of Ethyl 4'-(3-propylaminopropoxy)-3'-(5,5,8,8-tetramethyl-5,6,7,8-tetrahydronaphth-2-yl)biphenyl-4-carboxylate In a manner similar to that of Example 1c, by reaction of 1.3 ml (15.8 mmol) of n-propylamine and 960 mg (1.6 mmol)

of ethyl 4'-(3-iodopropoxy)-3'-(5,5,8,8-tetramethyl-5,6,7,8-tetrahydronaphth-2-yl)biphenyl-4-carboxylate (obtained in Example 1b) in 50 ml of ethanol. 790 mg of ethyl 4'-(3-propylaminopropoxy)-3'-(5,5,8,8-tetramethyl-5,6,7,8-tetrahydronaphth-2-yl)biphenyl-4-carboxylate are obtained in the form of a white solid (m.p.=120° C., yield=56%).

EXAMPLE 13

Synthesis of Compound 57

4'-(3-propylaminopropoxy)-3'-(5,5,8,8-tetramethyl-5,6,7,8-tetrahydronaphth-2-yl)biphenyl-4-carboxylic acid a) Synthesis of 4'-(3-Propylaminopropoxy)-3'-(5,5,8,8-tetramethyl-5,6,7,8-tetrahydronaphth-2-yl)biphenyl-4-carboxylic acid In a manner similar to that of Example 2a, by reaction of 584 mg (14.6 mmol) of sodium hydroxide with 770 mg (1.46 mmol) of ethyl 4'-(3-propylaminopropoxy)-3'-(5,5,8,8-tetramethyl-5,6,7,8-tetrahydronaphth-2-yl)biphenyl-4-carboxylate (Example 9a) in 30 ml of tetrahydrofuran. 470 mg of 4'-(3-propylaminopropoxy)-3'-(5,5,8,8-tetramethyl-5,6,7,8-tetrahydronaphth-2-yl)biphenyl-4-carboxylic acid are obtained in the form of a white solid (m.p.=226° C., yield=64%).

EXAMPLE 14

Synthesis of Compound 58

Ethyl 4'-(4-cyclopropylaminobutoxy)-3'-(5,5,8,8-tetramethyl-5,6,7,8-tetrahydronaphth-2-yl)biphenyl-4-carboxylate a) Preparation of Ethyl 4'-(4-Chlorobutoxy)-3'-(5,5,8,8-tetramethyl-5,6,7,8-tetrahydronaphth-2-yl)biphenyl-4-carboxylate 10 g (23 mmol) of ethyl 4'-hydroxy-3'-(5,5,8,8-tetramethyl-5,6,7,8-tetrahydronaphth-2-yl)biphenyl-4-carboxylate are dissolved in 400 ml of tetrahydrofuran. 9.2 g (35 mmol) of triphenylphosphine and 6.9 ml (35 mmol) of diisopropyl azodicarboxylate are added and the reaction medium is stirred at room temperature for 30 minutes. 2.8 ml (28 mmol) of 4-chlorobutanol are then added, and the medium is kept stirring for 12 hours, and then poured into 500 ml of water and extracted with ethyl acetate. The residue obtained is purified by chromatography on silica gel (eluent: 80/20 heptane/ethyl acetate). 8.9 g of ethyl 4'-(4-chlorobutoxy)-3'-(5,5,8,8-tetramethyl-5,6,7,8-tetrahydronaphth-2-yl)biphenyl-4-carboxylate are obtained in the form of a colorless oil (yield=73%).

b) Synthesis of Ethyl 4'-(2-cyclopropylaminobutoxy)-3'-(5,5,8,8-tetramethyl-5,6,7,8-tetrahydronaphth-2-yl)biphenyl-4-carboxylate In a manner similar to that of Example 1c, by reaction of 700 mg (1.3 mmol) of ethyl 4'-(4-chlorobutoxy)-3'-(5,5,8,8-tetramethyl-5,6,7,8-tetrahydronaphth-2-yl)biphenyl-4-carboxylate with 800 µl (11.5 mmol) of cyclopropylamine in 100 ml of ethanol. 180 mg of ethyl 4'-(2-cyclopropylaminobutoxy)-3'-(5,5,8,8-tetramethyl-5,6,7,8-tetrahydronaphth-2-yl)biphenyl-4-carboxylate are obtained in the form of a yellow oil (yield=26%).

$^1$H NMR (CDCl$_3$, 400 MHz): 0.31-0.33 (m, 2H); 0.41-0.44 (m, 2H); 1.42 (s, 12H); 1.43 (t, J=7.4 Hz, 3H); 1.60-1.64 (m, 2H); 1.75 (s, 4H); 1.82-1.86 (m, 2H); 2.07-2.10 (m, 1H); 2.72 (t, J=7.1 Hz, 2H); 4.06 (t, J=7.2 Hz, 2H); 4.42 (q, J=7.5 Hz, 2H); 7.07 (d, J=8.5 Hz, 1H); 7.28-7.39 (m, 2H); 7.55-7.60 (m, 2H); 7.64-7.69 (m, 3H); 8.10-8.12 (m, 2H).

EXAMPLE 15

Synthesis of Compound 59

4'-(4-Cyclopropylaminobutoxy)-3'-(5,5,8,8-tetramethyl-5,6,7,8-tetrahydronaphth-2-yl)biphenyl-4-carboxylic acid In a manner similar to that of Example 2a, by reaction of 130 mg (3 mmol) of sodium hydroxide with 180 mg (0.3 mmol) of ethyl 4'-(4-cyclopropylaminobutoxy)-3'-(5,5,8,8-tetramethyl-5,6,7,8-tetrahydronaphth-2-yl)biphenyl-4-carboxylate (Example 11) in 30 ml of tetrahydrofuran. 95 mg of 4'-(4-cyclopropylaminobutoxy)-3'-(5,5,8,8-tetramethyl-5,6,7,8-tetrahydronaphth-2-yl)biphenyl-4-carboxylic acid are obtained in the form of a white solid (m.p.=160° C., yield=62%).

EXAMPLE 16

Synthesis of Compound 60

Ethyl 4'-(3-methylaminopropoxy)-3'-(5,5,8,8-tetramethyl-5,6,7,8-tetrahydronaphth-2-yl)biphenyl-4-carboxylate a) Synthesis of Ethyl 4'-(3-methylaminopropoxy)-3'-(5,5,8,8-tetramethyl-5,6,7,8-tetrahydronaphth-2-yl)biphenyl-4-carboxylate In a manner similar to that of Example 1c, by reaction of 905 mg (13.4 mmol) of methylamine hydrochloride, 1.85 g (13.4 mmol) of potassium carbonate and 800 mg (1.34 mmol) of ethyl 4'-(3-iodopropoxy)-3'-(5,5,8,8-tetramethyl-5,6,7,8-tetrahydronaphth-2-yl)biphenyl-4-carboxylate (obtained in Example 1b) in 50 ml of ethanol. 511 mg of ethyl 4'-(3-methylaminopropoxy)-3'-(5,5,8,8-tetramethyl-5,6,7,8-tetrahydronaphth-2-yl)biphenyl-4-carboxylate are obtained in the form of a white solid (m.p.=141° C., yield=76%).

EXAMPLE 17

Synthesis of Compound 61

4'-(3-Methylaminopropoxy)-3'-(5,5,8,8-tetramethyl-5,6,7,8-tetrahydronaphth-2-yl)biphenyl-4-carboxylic acid a) Synthesis of 4'-(3-Methylaminopropoxy)-3'-(5,5,8,8-tetramethyl-5,6,7,8-tetrahydronaphth-2-yl)biphenyl-4-carboxylic acid In a manner similar to that of Example 2a, by reaction of 400 mg (10 mmol) of sodium hydroxide with 500 mg (1 mmol) of ethyl 4'-(3-methylaminopropoxy)-3'-(5,5,8,8-tetramethyl-5,6,7,8-tetrahydronaphth-2-yl)biphenyl-4-carboxylate (Example 13a) in 30 ml of tetrahydrofuran. 310 mg of 4'-(3-methylaminopropoxy)-3'-(5,5,8,8-tetramethyl-5,6,7,8-tetrahydronaphth-2-yl)biphenyl-4-carboxylic acid are obtained in the form of a white solid (m.p.=242° C., yield=66%).

EXAMPLE 18

Synthesis of Compound 62

Ethyl 4'-(3-ethylaminopropoxy)-3'-(5,5,8,8-tetramethyl-5,6,7,8-tetrahydronaphth-2-yl)biphenyl-4-carboxylate In a manner similar to that of Example 1c, by reaction of 1.1 g (13.4 mmol) of ethylamine hydrochloride, 1.85 g (13.4 mmol) of potassium carbonate and 800 mg (1.34 mmol) of ethyl 4'-(3-iodopropoxy)-3'-(5,5,8,8-tetramethyl-5,6,7,8-tetrahydronaphth-2-yl)biphenyl-4-carboxylate (obtained in Example 1b) in 50 ml of ethanol. 511 mg of ethyl 4'-(3-ethylaminopropoxy)-3'-(5,5,8,8-tetramethyl-5,6,7,8-tetrahydronaphth-2-yl)biphenyl-4-carboxylate are obtained in the form of a white solid (m.p.=148° C., yield=74%).

EXAMPLE 19

Synthesis of Compound 63

4'-(3-Ethylaminopropoxy)-3'-(5,5,8,8-tetramethyl-5,6,7,8-tetrahydronaphth-2-yl)biphenyl-4-carboxylic acid a) Synthesis of 4'-(3-Ethylaminopropoxy)-3'-(5,5,8,8-tetramethyl-5,6,7,8-tetrahydronaphth-2-yl)biphenyl-4-carboxylic acid In a manner similar to that of Example 2a, by reaction of 380 mg (9.5 mmol) of sodium hydroxide with 490 mg (0.95 mmol) of ethyl 4'-(3-ethylaminopropoxy)-3'-(5,5,8,8-tetramethyl-5,6,7,8-tetrahydronaphth-2-yl)biphenyl-4-carboxylate (Example 15a) in 30 ml of tetrahydrofuran. 395 mg of 4'-(3-ethylaminopropoxy)-3'-(5,5,8,8-tetramethyl-5,6,7,8-tetrahydronaphth-2-yl)biphenyl-4-carboxylic acid are obtained in the form of a white solid (m.p.=233° C., yield=85%).

EXAMPLE 20

Synthesis of Compound 64

Ethyl 4'-(3-aminopropoxy)-3'-(5,5,8,8-tetramethyl-5,6,7,8-tetrahydronaphth-2-yl)biphenyl-4-carboxylate a) Synthesis of Ethyl 4'-[3-(1,3-dioxo-1,3-dihydroisoindol-2-yl)propoxy]-3'-(5,5,8,8-tetramethyl-5,6,7,8-tetrahydronaphth-2-yl)biphenyl-4-carboxylate 600 mg (2.24 mmol) of N-(3-bromopropyl)phthalimide and 310 mg (2.24 mmol) of potassium carbonate are added to a solution of 800 mg (1.86 mmol) of ethyl 4'-hydroxy-3'-(5,5,8,8-tetramethyl-5,6,7,8-tetrahydronaphth-2-yl)biphenyl-4-carboxylate in 50 ml of acetone. The reaction mixture is stirred overnight at reflux. The reaction is stopped by adding water, and is then extracted with ethyl acetate. The organic phases are combined and dried over sodium sulfate. The solvents are evaporated off. The residue is precipitated from a small amount of ethyl acetate. It is filtered off and 700 mg of ethyl 4'-[3-(1,3-dioxo-1,3-dihydroisoindol-2-yl)propoxy]-3'-(5,5,8,8-tetramethyl-5,6,7,8-tetrahydronaphth-2-yl)biphenyl-4-carboxylate are obtained in the form of a white solid (yield=61%).

b) Synthesis of Ethyl 4'-(3-aminopropoxy)-3'-(5,5,8,8-tetramethyl-5,6,7,8-tetrahydronaphth-2-yl)biphenyl-4-carboxylate 100 μl of hydrazine monohydrate (2.05 mmol) are added to a solution of 650 mg (1 mmol) of ethyl 4'-[3-(1,3-dioxo-1,3-dihydroisoindol-2-yl)propoxy]-3'-(5,5,8,8-tetramethyl-5,6,7,8-tetrahydronaphth-2-yl)biphenyl-4-carboxylate in 50 ml of ethanol. The reaction mixture is stirred overnight at reflux. The reaction is stopped by adding water and hydrochloric acid to pH 4, and then extracted with ethyl acetate. The organic phases are combined and dried over sodium sulfate. The solvents are evaporated off. The residue is purified by chromatography on silica gel (eluent: 70/30 ethyl acetate/methanol). 180 mg of ethyl 4'-(3-aminopropoxy)-3'-(5,5,8,8-tetramethyl-5,6,7,8-tetrahydronaphth-2-yl)biphenyl-4-carboxylate are obtained in the form of a whitish solid (m.p.=155° C., yield=35%).

EXAMPLE 21

Synthesis of Compound 65

4'-(3-Aminopropoxy)-3'-(5,5,8,8-tetramethyl-5,6,7,8-tetrahydronaphth-2-yl)biphenyl-4-carboxylic acid a) Synthesis of 4'-(3-Aminopropoxy)-3'-(5,5,8,8-tetramethyl-5,6,7,8-tetrahydronaphth-2-yl)biphenyl-4-carboxylic acid In a manner similar to that of Example 2a, by reaction of 140 mg (3.5 mmol) of sodium hydroxide with 170 mg (0.35 mmol) of ethyl 4'-(3-aminopropoxy)-3'-(5,5,8,8-tetramethyl-5,6,7,8-tetrahydronaphth-2-yl)biphenyl-4-carboxylate (Example 17b) in 30 ml of tetrahydrofuran. 95 mg of 4'-(3-aminopropoxy)-3'-(5,5,8,8-tetramethyl-5,6,7,8-tetrahydronaphth-2-yl)biphenyl-4-carboxylic acid are obtained in the form of a white solid (m.p.=243° C., yield=49%).

EXAMPLE 22

Synthesis of Compound 66

Ethyl 4'-(2-cyclopropylaminoethoxy)-3'-(5,5,8,8-tetramethyl-5,6,7,8-tetrahydronaphth-2-yl)biphenyl-4-carboxylate a) Preparation of Ethyl 4'-(2-bromoethoxy)-3'-(5,5,8,8-tetramethyl-5,6,7,8-tetrahydronaphth-2-yl)biphenyl-4-carboxylate In a manner similar to that of Example 1a, by reaction of 6 g (14 mmol) of ethyl 4'-hydroxy-3'-(5,5,8,8-tetramethyl-5,6,7,8-tetrahydronaphth-2-yl)biphenyl-4-carboxylate with 4 ml (46.2 mmol) of 1,2-dibromoethane. 2.12 g of ethyl 4'-(2-bromoethoxy)-3'-(5,5,8,8-tetramethyl-5,6,7,8-tetrahydronaphth-2-yl)biphenyl-4-carboxylate are obtained in the form of a white solid (yield=28%).

b) Synthesis of Ethyl 4'-2-cyclopropylaminoethoxy)-3'-(5,5,8,8-tetramethyl-5,6,7,8-tetrahydronaphth-2-yl)biphenyl-4-carboxylate In a manner similar to that of Example 1c, by reaction of 600 mg (1.15 mmol) of ethyl 4'-(2-bromoethoxy)-3'-(5,5,8,8-tetramethyl-5,6,7,8-tetrahydronaphth-2-yl)biphenyl-4- carboxylate with 800 µl (11.5 mmol) of cyclopropylamine in 100 ml of ethanol. 360 mg of ethyl 4'-(2-cyclopropylaminoethoxy)-3'-(5,5,8,8-tetramethyl-5,6,7,8-tetrahydronaphth-2-yl)biphenyl-4-carboxylate are obtained in the form of a white solid (m.p.=141° C., yield=63%).

EXAMPLE 23

Synthesis of Compound 67

4'-(2-Cyclopropylaminoethoxy)-3'-(5,5,8,8-tetramethyl-5,6,7,8-tetrahydronaphth-2-yl)biphenyl-4-carboxylic acid a) Synthesis of 4'-(2-Cyclopropylaminoethoxy)-3'-(5,5,8,8-tetramethyl-5,6,7,8-tetrahydronaphth-2-yl)biphenyl-4-carboxylic acid In a manner similar to that of Example 2a, by reaction of 270 mg (6.75 mmol) of sodium hydroxide with 340 mg (0.66 mmol) of ethyl 4'-(3-cyclopropylaminoethoxy)-3'-(5,5,8,8-tetramethyl-5,6,7,8-tetrahydronaphth-2-yl)biphenyl-4-carboxylate (Example 19b) in 30 ml of tetrahydrofuran. 240 mg of 4'-(3-cyclopropylaminoethoxy)-3'-(5,5,8,8-tetramethyl-5,6,7,8-tetrahydronaphth-2-yl)biphenyl-4-carboxylic acid are obtained in the form of a white solid (m.p.=233° C., yield=75%).

EXAMPLE 24

Synthesis of Compound 68

Ethyl 4'-(5-cyclopropylaminopentyloxy)-3'-(5,5,8,8-tetramethyl-5,6,7,8-tetrahydronaphth-2-yl)biphenyl-4-carboxylate a) Preparation of Ethyl 4'-(5-bromopentyloxy)-3'-(5,5,8,8-tetramethyl-5,6,7,8-tetrahydronaphth-2-yl)biphenyl-4-carboxylate In a manner similar to that of Example 1a, by reaction of 5 g (11.6 mmol) of ethyl 4'-hydroxy-3'-(5,5,8,8-tetramethyl-5,6,7,8-tetrahydronaphth-2-yl)biphenyl-4-carboxylate with 5.2 ml (38.5 mmol) of 1,5-dibromopentane. 4.7 g of ethyl 4'-(5-bromopentyloxy)-3'-(5,5,8,8-tetramethyl-5,6,7,8-tetrahydronaphth-2-yl)biphenyl-4-carboxylate are obtained in the form of a white solid (yield=70%).

b) Synthesis of Ethyl 4'-(5-cyclopropylaminopentyloxy)-3'-(5,5,8,8-tetramethyl-5,6,7,8-tetrahydronaphth-2-yl)biphenyl-4-carboxylate In a manner similar to that of Example 1b, by reaction of 600 mg (1 mmol) of ethyl 4'-(5-bromopentyloxy)-3'-(5,5,8,8-tetramethyl-5,6,7,8-tetrahydronaphth-2-yl)biphenyl-4-carboxylate with 720 µl (11.5 mmol) of cyclopropylamine in 50 ml of ethanol. 420 mg of ethyl 4'-(5-cyclopropylaminopentyloxy)-3'-(5,5,8,8-tetramethyl-5,6,7,8-tetrahydronaphth-2-yl)biphenyl-4-carboxylate are obtained in the form of a white paste (yield=73%).

$^1$H NMR (CDCl$_3$, 400 MHz): 0.72-0.75 (m, 2H); 1.02-1.04 (m, 2H); 1.35 (s, 12H); 1.43 (t, J=7.6 Hz, 3H); 1.50-1.54 (m, 2H); 1.75 (s, 4H); 1.80-1.87 (m, 4H); 2.41-2.45 (m, 1H); 2.93 (t, J=7.8 Hz, 2H); 4.15 (t, J=7.4 Hz, 2H); 4.41 (q, J=7.6 Hz, 2H); 7.05 (d, J=8.2 Hz, 1H); 7.31-7.39 (m, 2H); 7.51-7.58 (m, 2H); 7.62-7.67 (m, 3H); 8.09-8.11 (m, 2H).

EXAMPLE 25

Synthesis of Compound 69

4'-(5-Cyclopropylaminopentyloxy)-3'-(5,5,8,8-tetramethyl-5,6,7,8-tetrahydronaphth-2-yl)biphenyl-4-carboxylic acid a) Synthesis of 4'-(5-Cyclopropylaminopentyloxy)-3'-(5,5,8,8-tetramethyl-5,6,7,8-tetrahydronaphth-2-yl)biphenyl-4-carboxylic acid In a manner similar to that of Example 2a, by reaction of 300 mg (7.5 mmol) of sodium hydroxide with 410 mg (0.74 mmol) of ethyl 4'-(3-cyclopropylaminopentyloxy)-3'-(5,5,8,8-tetramethyl-5,6,7,8-tetrahydronaphth-2-yl)biphenyl-4-carboxylate (Example 21b) in 30 ml of tetrahydrofuran. 290 mg of 4'-(3-cyclopropylaminopentyloxy)-3'-(5,5,8,8-tetramethyl-5,6,7,8-tetrahydronaphth-2-yl)biphenyl-4-carboxylic acid are obtained in the form of a white solid (m.p.=161° C., yield=75%).

EXAMPLE 26

Synthesis of Compound 70

Ethyl 4'-(2-isopropylaminoethoxy)-3'-(5,5,8,8-tetramethyl-5,6,7,8-tetrahydronaphth-2-yl)biphenyl-4-carboxylate a) Synthesis of Ethyl 4'-(2-isopropylaminoethoxy)-3'-(5,5,8,8-tetramethyl-5,6,7,8-tetrahydronaphth-2-yl)biphenyl-4-carboxylate In a manner similar to that of Example 1b, by reaction of 420 mg (0.78 mmol) of ethyl 4'-(5-bromoethoxy)-3'-(5,5,8,8-tetramethyl-5,6,7,8-tetrahydronaphth-2-yl)biphenyl-4-carboxylate (Example 19a) with 670 µl (7.86 mmol) of isopropylamine in 50 ml of ethanol. 250 mg of ethyl 4'-(5-isopropylaminoethoxy)-3'-(5,5,8,8-tetramethyl-5,6,7,8-tetrahydronaphth-2-yl)biphenyl-4-carboxylate are obtained in the form of a white solid (m.p.=104° C., yield=62%).

EXAMPLE 27

Synthesis of Compound 71

Ethyl 4'-(5-ethylaminopentyloxy)-3'-(5,5,8,8-tetramethyl-5,6,7,8-tetrahydronaphth-2-yl)biphenyl-4-carboxylate a) Synthesis of Ethyl 4'-(5-ethylaminopentyloxy)-3'-(5,5,8,8-tetramethyl-5,6,7,8-tetrahydronaphth-2-yl)biphenyl-4-carboxylate In a manner similar to that of Example 1b, by reaction of 600 mg (1 mmol) of ethyl 4'-(5-bromopentyloxy)-3'-(5,5,8,8-tetramethyl-5,6,7,8-tetrahydronaphth-2-yl)biphenyl-4-carboxylate with 850 mg (10.4 mmol) of ethylamine hydrochloride and 1.44 g (10.4 mmol) of potassium carbonate in 50 ml of ethanol. 350 mg of ethyl 4'-(5-ethylaminopentyloxy)-3'-(5,5,8,8-tetramethyl-5,6,7,8-tetrahydronaphth-2-yl)biphenyl-4-carboxylate are obtained in the form of a colorless oil (yield=62%).

$^1$H NMR (CDCl$_3$, 400 MHz): 1.14 (t, J=7.3 Hz, 3H); 1.35 (s, 12H); 1.43 (t, J=7.6 Hz, 3H); 1.50-1.56 (m, 4H); 1.75 (s, 4H); 1.79-1.85 (m, 2H); 2.61-2.71 (m, 4H); 4.05 (t, J=7.4 Hz,

2H); 4.42 (q, J=7.6 Hz, 2H); 7.06 (d, J=8.2 Hz, 1H); 7.33-7.39 (m, 2H); 7.54-7.68 (m, 5H); 8.09-8.12 (m, 2H).

EXAMPLE 28

Synthesis of Compound 72

Ethyl 4'-(5-aminopentyloxy)-3'-(5,5,8,8-tetramethyl-5,6,7,8-tetrahydronaphth-2-yl)biphenyl-4-carboxylate a) Preparation of Ethyl 4'-[5-(1,3-dioxo-1,3-dihydroisoindol-2-yl)pentyloxy]-3'-(5,5,8,8-tetramethyl-5,6,7,8-tetrahydronaphth-2-yl)biphenyl-4-carboxylate In a manner similar to that of Example 17a, by reaction of 600 mg (1.4 mmol) of ethyl 4'-hydroxy-3'-(5,5,8,8-tetramethyl-5,6,7,8-tetrahydronaphth-2-yl)biphenyl-4-carboxylate with 500 mg (1.7 mmol) of N-(5-bromopentyl)phthalimide and 230 mg (1.66 mmol) of potassium carbonate in 50 ml of acetone. 770 mg of ethyl 4'-[5-(1,3-dioxo-1,3-dihydroisoindol-2-yl)pentyloxy]-3'-(5,5,8,8-tetramethyl-5,6,7,8-tetrahydronaphth-2-yl)biphenyl-4-carboxylate are obtained in the form of a beige-colored solid (yield=85%).

b) Synthesis of Ethyl 4'-(5-aminopentyloxy)-3'-(5,5,8,8-tetramethyl-5,6,7,8-tetrahydronaphth-2-yl)biphenyl-4-carboxylate In a manner similar to that of Example 17b, by reaction of 760 mg (1.18 mmol) of ethyl 4'-[5-(1,3-dioxo-1,3-dihydroisoindol-2-yl)pentyloxy]-3'-(5,5,8,8-tetramethyl-5,6,7,8-tetrahydronaphth-2-yl)biphenyl-4-carboxylate with 230 µl (4.72 mmol) of hydrazine monohydrate in 50 ml of ethanol. 280 mg of ethyl 4'-(5-aminopentyloxy)-3'-(5,5,8,8-tetramethyl-5,6,7,8-tetrahydronaphth-2-yl)biphenyl-4-carboxylate are obtained in the form of a whitish solid (yield=46%).

$^1$H NMR (CDCl$_3$, 400 MHz): 1.32 (s, 6H); 1.33 (s, 6H); 1.43 (t, J=7.5 Hz, 3H); 1.53-1.58 (m, 2H); 1.73 (s, 4H); 1.77-1.81 (m, 4H); 2.97 (t, J=7.8 Hz, 2H); 4.00 (t, J=7.4 Hz, 2H); 4.41 (q, J=7.6 Hz, 2H); 7.02 (d, J=8.2 Hz, 1H); 7.31-7.38 (m, 2H); 7.51-7.55 (m, 2H); 7.61-7.65 (m, 3H); 8.08-8.11 (m, 2H).

EXAMPLE 29

Synthesis of Compound 73

4'-(5-Aminopentyloxy)-3'-(5,5,8,8-tetramethyl-5,6,7,8-tetrahydronaphth-2-yl)biphenyl-4-carboxylic acid a) Synthesis of 4'-(5-Aminopentyloxy)-3'-(5,5,8,8-tetramethyl-5,6,7,8-tetrahydronaphth-2-yl)biphenyl-4-carboxylic acid In a manner similar to that of Example 2a, by reaction of 210 mg (5.2 mmol) of sodium hydroxide with 270 mg (0.52 mmol) of ethyl 4'-(5-aminopentyloxy)-3'-(5,5,8,8-tetramethyl-5,6,7,8-tetrahydronaphth-2-yl)biphenyl-4-carboxylate (Example 27b) in 30 ml of tetrahydrofuran. 165 mg of 4'-(3-ethylaminopentyloxy)-3'-(5,5,8,8-tetramethyl-5,6,7,8-tetrahydronaphth-2-yl)biphenyl-4-carboxylic acid are obtained in the form of a white solid (m.p.=252° C., yield=65%).

EXAMPLE 30

Synthesis of Compound 74

Ethyl 4'-(4-aminobutoxy)-3'-(5,5,8,8-tetramethyl-5,6,7,8-tetrahydronaphth-2-yl)biphenyl-4-carboxylate a) Preparation of Ethyl 4'-[4-(1,3-dioxo-1,3-dihydroisoindol-2-yl)butoxy]-3'-(5,5,8,8-tetramethyl-5,6,7,8-tetrahydronaphth-2-yl)biphenyl-4-carboxylate In a manner similar to that of Example 17a, by reaction of 600 mg (1.4 mmol) of ethyl 4'-hydroxy-3'-(5,5,8,8-tetramethyl-5,6,7,8-tetrahydronaphth-2-yl)biphenyl-4-carboxylate with 475 mg (1.68 mmol) of N-(4-bromobutoxy)phthalimide and 230 mg (1.66 mmol) of potassium carbonate in 50 ml of acetone. 790 mg of ethyl 4'-[4-(1,3-dioxo-1,3-dihydroisoindol-2-yl)butoxy]-3'-(5,5,8,8-tetramethyl-5,6,7,8-tetrahydronaphth-2-yl)biphenyl-4-carboxylate are obtained in the form of a white solid (yield=90%).

b) Synthesis of Ethyl 4'-(4-aminobutoxy)-3'-(5,5,8,8-tetramethyl-5,6,7,8-tetrahydronaphth-2-yl)biphenyl-4-carboxylate In a manner similar to that of Example 17b, by reaction of 750 mg (1.19 mmol) of ethyl 4'-[4-(1,3-dioxo-1,3-dihydroisoindol-2-yl)butoxy]-3'-(5,5,8,8-tetramethyl-5,6,7,8-tetrahydronaphth-2-yl)biphenyl-4-carboxylate with 230 µl (4.72 mmol) of hydrazine monohydrate in 50 ml of ethanol. 300 mg of 4'-(4-aminobutoxy)-3'-(5,5,8,8-tetramethyl-5,6,7,8-tetrahydronaphth-2-yl)biphenyl-4-carboxylate are obtained in the form of a yellow-brown solid (yield=50%).

$^1$H NMR (CDCl$_3$, 400 MHz): 1.33 (s, 6H); 1.34 (s, 6H); 1.43 (t, J=7.5 Hz, 3H); 1.73 (s, 4H); 1.73-1.75 (m, 2H); 1.85-1.89 (m, 2H); 2.84 (t, J=7.4 Hz, 2H); 3.30 (bs, 2H); 4.04 (t, J=7.4 Hz, 2H); 4.41 (q, J=7.6 Hz, 2H); 7.03 (d, J=8.2 Hz, 1H); 7.31-7.40 (m, 2H); 7.52-7.55 (m, 2H); 7.61-7.66 (m, 3H); 8.09-8.11 (m, 2H).

EXAMPLE 31

Synthesis of Compound 75

4'-(4-Aminobutoxy)-3'-(5,5,8,8-tetramethyl-5,6,7,8-tetrahydronaphth-2-yl)biphenyl-4-carboxylic acid a) Synthesis of 4'-(4-Aminobutoxy)-3'-(5,5,8,8-tetramethyl-5,6,7,8-tetrahydronaphth-2-yl)biphenyl-4-carboxylic acid In a manner similar to that of Example 2a, by reaction of 300 mg (0.6 mmol) of ethyl 4'-(4-aminobutoxy)-3'-(5,5,8,8-tetramethyl-5,6,7,8-tetrahydronaphth-2-yl)biphenyl-4-carboxylate with 240 mg (6 mmol) of sodium hydroxide. 245 mg of 4'-(4-aminobutoxy)-3'-(5,5,8,8-tetramethyl-5,6,7,8-tetrahydronaphth-2-yl)biphenyl-4-carboxylic acid are obtained in the form of a white solid (m.p.=250° C., yield=86%).

EXAMPLE 32

Transactivation Test

The activation of receptors with an agonist (activator) in HeLa cells leads to the expression of a reporter gene, luciferase, which, in the presence of a substrate, generates light. The activation of the receptors may thus be measured by quantifying the luminescence produced after incubating the cells in the presence of a reference agonist. The activating products displace the agonist from its site, thus preventing activation of the receptor. The activity is measured by quantifying the decrease in light produced. This measurement makes it possible to determine the activating activity of the compounds according to the invention.

In this study, a constant is determined which represents the affinity of the molecule for the receptor. Since this value can fluctuate depending on the basal activity and the expression of the receptor, it is referred to as the Kd apparent (KdApp).

To determine this constant, the cells are brought into contact with a concentration of the test product and a concentration of the reference antagonist, 4-(5,5-dimethyl-8-p-tolyl-5, 6-dihydro-2-naphthalen-2-ylethynyl)benzoic acid. Measurements are also taken for the total agonist (4-[2-(5,5, 8,8-tetramethyl-5,6,7,8-tetrahydro-2-naphthyl)propenyl] benzoic acid) and inverse agonist, 4-{(E)-3-[4-(4-tert-butylphenyl)-5,5,8,8-tetramethyl-5,6,7,8-tetrahydro-2-naphthyl]-3-oxopropenyl}benzoic acid, controls.

These crossed curves make it possible to determine the $AC_{50}$ values (concentration at which 50% activation is observed) for the reference ligand at various concentrations of test product. These $AC_{50}$ values are used to calculate the Schild regression by plotting a straight line corresponding to the Schild equation ("Quantitation in Receptor Pharmacology" Terry P. Kenakin, *Receptors and Channels*, 2001, 7, 371-385).

In the case of an agonist, an $AC_{50}$ value (concentration that gives 50% of the activity) is calculated by plotting the curve of the product at the concentration of the reference ligand that gives 80% activation.

The HeLa cell lines used are stable transfectants containing the plasmids ERE-βGlob-Luc-SV-Neo (reporter gene) and RAR (α, β, γ) ER-DBD-puro. These cells are inoculated into 96-well plates at a rate of 10,000 cells per well in 100 µl of DMEM medium without phenol red, and supplemented with 10% defatted calf serum. The plates are then incubated at 37° C. and 7% $CO_2$ for 4 hours.

The various dilutions of the test products, of the reference ligand (4-(5,5-dimethyl-8-p-tolyl-5,6-dihydro-2-naphthalen-2-ylethynyl)benzoic acid), of the 100% control (100 nM 4-[2-(5,5,8,8-tetramethyl-5,6,7,8-tetrahydro-2-naphthyl) propenyl]benzoic acid) and of the 0% control (500 nM 4-{ (E)-3-[4-(4-tert-butylphenyl)-5,5,8,8-tetramethyl-5,6,7,8-tetrahydro-2-naphthyl]-3-oxopropenyl}benzoic acid) are added at a rate of 5 µl per well. The plates are then incubated for 18 hours at 37° C. and 7% $CO_2$.

The culture medium is removed by turning over and 100 µl of a 1:1 PBS/luciferin mixture is added to each well. After 5 minutes, the plates are read using the luminescence reader.

| compound | RAR alpha KD app (nM) | RAR beta Kd app (nM) | RAR gamma Kd app (nM) |
|---|---|---|---|
| 1 | 1000 | 500 | 15 |
| 59 | 8000 | 4000 | 1000 |
| 61 | 9999 | 9999 | 30 |
| 63 | nd | nd | 250 |
| 65 | nd | nd | 8 |
| 67 | 1000 | 60 | 4 |
| 69 | 2000 | 500 | 250 |
| 12 | 9999 | 4000 | 120 |

-continued

| compound | RAR alpha KD app (nM) | RAR beta Kd app (nM) | RAR gamma Kd app (nM) |
|---|---|---|---|
| 73 | 2000 | 2000 | 120 |
| 75 | 8000 | 2000 | 60 |

Nd: not determined

The results obtained with the compounds according to the invention clearly show Kd app values ≦100 nM for at least one of the receptor subtypes, this clearly demonstrating an increase in the signal, and in the luminescence in the presence of the reference antagonist. The compounds according to the invention are thus clearly activators of retinoic acid receptors (RAR).

EXAMPLE 33

Formulation Examples

This example illustrates various specific formulations based on the compounds according to the invention.

A - ORAL ROUTE:

(a) 0.2 g Tablet:

| | |
|---|---|
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable suspension in 5 ml ampoules:

| | |
|---|---|
| Compound of Example 1 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavoring | qs |
| Purified water | qs 5 ml |

(c) 0.8 g Tablet:

| | |
|---|---|
| Compound of Example 1 | 0.500 g |
| Pregelatinized starch | 0.100 g |
| Microcrystalline cellulose | 0.115 g |
| Lactose | 0.075 g |
| Magnesium stearate | 0.010 g |

(d) Drinkable suspension in 10 ml ampoules:

| | |
|---|---|
| Compound of Example 1 | 0.200 g |
| Glycerol | 1.000 g |
| 70% sorbitol | 1.000 g |
| Sodium saccharinate | 0.010 g |
| Methyl para-hydroxybenzoate | 0.080 g |
| Flavoring | qs |
| Purified water | qs 10 ml |

B - PARENTERAL ROUTE:

(a) Composition:

| | |
|---|---|
| Compound of Example 1 | 0.002 g |
| Ethyl oleate | qs 10 g |

(b) Composition:

| | |
|---|---|
| Compound of Example 1 | 0.05% |
| Polyethylene glycol | 20% |
| 0.9% NaCl solution | qs 100 |

-continued

| (c) Composition: | |
|---|---|
| Compound of Example 1 | 2.5% |
| Polyethylene glycol 400 | 20% |
| 0.9% NaCl solution | qs 100 |
| (d) Injectable cyclodextrin composition: | |
| Compound of Example 1 | 0.1 mg |
| β-Cyclodextrin | 0.10 g |
| Water for injection | qs 10.00 g |
| C - TOPICAL ROUTE: | |
| (a) Ointment: | |
| Compound of Example 1 | 0.020 g |
| Isopropyl myristate | 81.700 g |
| Liquid petroleum jelly oil | 9.100 g |
| Silica ("Aerosil 200" marketed by Degussa) | 9.180 g |
| (b) Ointment: | |
| Compound of Example 1 | 0.300 g |
| White petroleum jelly codex | qs 100 g |
| (c) Nonionic water-in-oil cream: | |
| Compound of Example 4 | 0.100 g |
| Mixture of emulsifying lanolin alcohols, waxes and oils ("Anhydrous Eucerin" marketed by BDF) | 39.900 g |
| Methyl para-hydroxybenzoate | 0.075 g |
| Propyl para-hydroxybenzoate | 0.075 g |
| Sterile demineralized water | qs 100 g |
| (d) Lotion: | |
| Compound of Example 1 | 0.100 g |
| Polyethylene glycol (PEG 400) | 69.900 g |
| 95% ethanol | 30.000 g |
| (e) Hydrophobic ointment: | |
| Compound of Example 1 | 0.300 g |
| Isopropyl myristate | 36.400 g |
| Silicone oil ("Rhodorsil 47 V 300" marketed by Rhône-Poulenc) | 36.400 g |
| Beeswax | 13.600 g |
| Silicone oil ("Abil 300 000 cst" marketed by Goldschmidt) | qs 100 g |
| (f) Nonionic oil-in-water cream: | |
| Compound of Example 1 | 1.000 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A compound having the following structural formula:

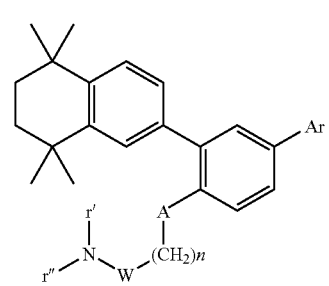

(I)

in which:
Ar is a radical selected from among the radicals of formulae (a) to (c) below:

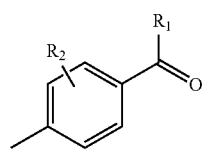

a)

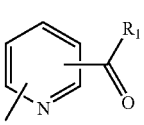

b)

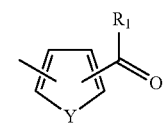

c)

wherein $R_1$ is a radical —$OR_3$ or —$NR_4R_5$ and $R_3$, $R_4$ and $R_5$ are as defined below, wherein $R_2$ is a hydrogen, fluorine or chlorine atom, a methyl radical or a radical $OR_6$ and $R_6$ is as defined below;

$R_3$ is a hydrogen atom, a linear or branched alkyl radical having from 1 to 20 carbon atoms, a mono- or polyhydroxyalkyl radical having from 1 to 20 carbon atoms, a monoaminoalkyl radical having from 1 to 20 carbon atoms, or a sugar residue;

$R_4$ and $R_5$, which may be identical or different, are each a hydrogen atom, a hydroxyl radical, a linear or branched alkyl radical having from 1 to 6 carbon atoms, a mono- or polyhydroxyalkyl radical having from 1 to 20 carbon atoms, or $R_4$ and $R_5$ together form, with the nitrogen atom from which they depend, an amino acid residue or a peptide residue, or, alternatively, $R_4$ and $R_5$ together form with said nitrogen atom a heterocycle;

$R_6$ is a hydrogen atom, a methyl radical or an acetyl radical;

$R_7$ is $CF_3$ or a methyl radical;

r' and r", which may be identical or different, are each a hydrogen atom, a linear, branched or cyclic alkyl radical having from 1 to 4 carbon atoms, or a radical (C=O)$R_7$, or, alternatively, r' and r" with the nitrogen atom from which they depend, together form a pyrrolidine or piperidine;

A is an oxygen atom or a sulfur atom;

n is an integer ranging from 1 and 4;

W is a —CH$_2$— radical;

Y is an oxygen atom or a sulfur atom;

or a salt of the compound of formula (I) when R$_1$=OH, or an optical or geometrical isomer of the compound of formula (I).

2. The compound as defined by claim 1, wherein formula (I), Ar is a radical a).

3. The compound as defined by claim 1, wherein formula (I), Ar is a radical b).

4. The compound as defined by claim 1, wherein formula (I), Ar is a radical c).

5. The compound as defined by claim 1, wherein formula (I), A is oxygen.

6. An alkali metal or alkaline-earth metal, zinc or organic amine salt of the compound as defined by claim 1.

7. The compound as defined by claim 1, wherein at least one of R$_4$ and R$_5$ is selected from the group consisting of methyl, ethyl, n-propyl, isopropyl, cyclopropyl, n-butyl, i-butyl, t-butyl, n-pentyl and n-hexyl radicals.

8. The compound as defined by claim 1, wherein R$_3$ is selected from the group consisting of methyl, ethyl, n-propyl, isopropyl, cyclopropyl, n-butyl, i-butyl, t-butyl, n-pentyl, n-hexyl, 2-ethylhexyl, octyl, dodecyl, hexadecyl and octadecyl radicals.

9. The compound as defined by claim 1, bearing at least one substituent selected from the group consisting of 2-hydroxyethyl, 2-hydroxypropyl and 3-hydroxypropyl radicals.

10. The compound as defined by claim 1, bearing at least one substituent selected from the group consisting of 2,3-dihydroxypropyl, 2,3,4-trihydroxybutyl and 2,3,4,5-tetrahydroxypentyl radicals, or a pentaerythritol residue.

11. The compound as defined by claim 1, bearing at least one substituent selected from the group consisting of methyl, ethyl, n-propyl, isopropyl, cyclopropyl, n-butyl, i-butyl and t-butyl radicals.

12. The compound as defined by claim 1, bearing at least one substituent selected from the group consisting of residues derived from glucose, galactose, mannose and glucuronic acid.

13. The compound as defined by claim 1, bearing at least one substituent selected from the group consisting of residues derived from lysine, glycine and aspartic acid.

14. The compound as defined by claim 1, bearing at least one substituent selected from the group consisting of dipeptide and tripeptide residues resulting from the combination of amino acids.

15. The compound as defined by claim 1, wherein at least one of the following conditions is satisfied:

Ar is a radical (a),

A is an oxygen atom,

R$_1$ is a radical OR$_3$.

16. The compound as defined by claim 1, selected from the group consisting of:

1. 4'-(4-Isopropylaminobutoxy)-3'-(5,5,8,8-tetramethyl-5,6,7,8-tetrahydronaphth-2-yl)biphenyl-4-carboxylic acid;
2. 4'-(4-Ethylaminobutoxy)-3'-(5,5,8,8-tetramethyl-5,6,7,8-tetrahydronaphth-2-yl)biphenyl-4-carboxylic acid;
3. 4'-(4-Propylaminobutoxy)-3'-(5,5,8,8-tetramethyl-5,6,7,8-tetrahydronaphth-2-yl)biphenyl-4-carboxylic acid;
4. 4'-[4-(Isopropylmethylamino)butoxy]-3'-(5,5,8,8-tetramethyl-5,6,7,8-tetrahydronaphth-2-yl)biphenyl-4-carboxylic acid;
5. 4'-(4-Diethylaminobutoxy)-3'-(5,5,8,8-tetramethyl-5,6,7,8-tetrahydronaphth-2-yl)biphenyl-4-carboxylic acid;
6. 4'-(4-Acetylaminobutoxy)-3'-(5,5,8,8-tetramethyl-5,6,7,8-tetrahydronaphth-2-yl)biphenyl-4-carboxylic acid;
7. 4'-[4-(Acetylethylamino)butoxy]-3'-(5,5,8,8-tetramethyl-5,6,7,8-tetrahydronaphth-2-yl)biphenyl-4-carboxylic acid;
8. 4'-[4-(Acetylisopropylamino)butoxy]-3'-(5,5,8,8-tetramethyl-5,6,7,8-tetrahydronaphth-2-yl)biphenyl-4-carboxylic acid;
9. 4'-(4-Acetylaminobutoxy)-3'-(5,5,8,8-tetramethyl-5,6,7,8-tetrahydronaphth-2-yl)biphenyl-4-carboxylic acid;
10. 4'-(4-Pyrrolidin-1-ylbutoxy)-3'-(5,5,8,8-tetramethyl-5,6,7,8-tetrahydronaphth-2-yl)biphenyl-4-carboxylic acid;
11. 4'-(4-Isopropylaminobutylsulfanyl)-3'-(5,5,8,8-tetramethyl-5,6,7,8-tetrahydronaphth-2-yl)biphenyl-4-carboxylic acid;
12. 4'-(2-Isopropylaminoethoxy)-3'-(5,5,8,8-tetramethyl-5,6,7,8-tetrahydronaphth-2-yl)biphenyl-4-carboxylic acid;
13. 4'-(3-Isopropylaminopropoxy)-3'-(5,5,8,8-tetramethyl-5,6,7,8-tetrahydronaphth-2-yl)biphenyl-4-carboxylic acid;
14. 4'-(5-Isopropylaminopentyloxy)-3'-(5,5,8,8-tetramethyl-5,6,7,8-tetrahydronaphth-2-yl)biphenyl-4-carboxylic acid;
15. 4'-(5-Ethylaminopentyloxy)-3'-(5,5,8,8-tetramethyl-5,6,7,8-tetrahydronaphth-2-yl)biphenyl-4-carboxylic acid;
16. Ethyl 4'-(4-isopropylaminobutoxy)-3'-(5,5,8,8-tetramethyl-5,6,7,8-tetrahydronaphth-2-yl)biphenyl-4-carboxylate;
17. Propyl 4'-(4-isopropylaminobutoxy)-3'-(5,5,8,8-tetramethyl-5,6,7,8-tetrahydronaphth-2-yl)biphenyl-4-carboxylate;
18. Isopropyl 4'-(4-isopropylaminobutoxy)-3'-(5,5,8,8-tetramethyl-5,6,7,8-tetrahydronaphth-2-yl)biphenyl-4-carboxylate;
19. 2,3-Dihydroxypropyl 4'-(4-isopropylaminobutoxy)-3'-(5,5,8,8-tetramethyl-5,6,7,8-tetrahydronaphth-2-yl)biphenyl-4-carboxylate;
20. 3-Aminopropyl 4'-(4-isopropylaminobutoxy)-3'-(5,5,8,8-tetramethyl-5,6,7,8-tetrahydronaphth-2-yl)biphenyl-4-carboxylate;
21. 6-Glucosyl 4'-(4-isopropylaminobutoxy)-3'-(5,5,8,8-tetramethyl-5,6,7,8-tetrahydronaphth-2-yl)biphenyl-4-carboxylate;
22. 6-Mannosyl 4'-(4-isopropylaminobutoxy)-3'-(5,5,8,8-tetramethyl-5,6,7,8-tetrahydronaphth-2-yl)biphenyl-4-carboxylate;
23. Ethyl 4'-(4-isopropylaminobutoxy)-3'-(5,5,8,8-tetramethyl-5,6,7,8-tetrahydronaphth-2-yl)biphenyl-4-carboxamide;
24. Diethyl 4'-(4-isopropylaminobutoxy)-3'-(5,5,8,8-tetramethyl-5,6,7,8-tetrahydronaphth-2-yl)biphenyl-4-carboxamide;
25. [4'-(4-Isopropylaminobutoxy)-3'-(5,5,8,8-tetramethyl-5,6,7,8-tetrahydronaphth-2-yl)biphenyl-4-yl]pyrrolidin-1-ylmethanone;
26. {[4'-(4-Isopropylaminobutoxy)-3'-(5,5,8,8-tetramethyl-5,6,7,8-tetrahydronaphth-2-yl)biphenyl-4-carbonyl]amino}acetic acid;
27. 3-Hydroxy-2-{[4'-(4-isopropylaminobutoxy)-3'-(5,5,8,8-tetramethyl-5,6,7,8-tetrahydronaphth-2-yl)biphenyl-4-carbonyl]amino}propionic acid;
28. 3-Fluoro-4'-(4-isopropylaminobutoxy)-3'-(5,5,8,8-tetramethyl-5,6,7,8-tetrahydronaphth-2-yl)biphenyl-4-carboxylic acid;

29. 3-Chloro-4'-(4-isopropylaminobutoxy)-3'-(5,5,8,8-tetramethyl-5,6,7,8-tetrahydronaphth-2-yl)biphenyl-4-carboxylic acid;
30. 3-Chloro-4'-(4-isopropylaminobutoxy)-3'-(5,5,8,8-tetramethyl-5,6,7,8-tetrahydronaphth-2-yl)biphenyl-4-carboxylic acid;
31. 3-Hydroxy-4'-(4-isopropylaminobutoxy)-3'-(5,5,8,8-tetramethyl-5,6,7,8-tetrahydronaphth-2-yl)biphenyl-4-carboxylic acid;
32. 4'-(4-Isopropylaminobutoxy)-3-methoxy-3'-(5,5,8,8-tetramethyl-5,6,7,8-tetrahydronaphth-2-yl)biphenyl-4-carboxylic acid;
33. 3-Acetoxy-4'-(4-isopropylaminobutoxy)-3'-(5,5,8,8-tetramethyl-5,6,7,8-tetrahydronaphth-2-yl)biphenyl-4-carboxylic acid;
34. 2-Fluoro-4'-(4-isopropylaminobutoxy)-3'-(5,5,8,8-tetramethyl-5,6,7,8-tetrahydronaphth-2-yl)biphenyl-4-carboxylic acid;
35. 2-Chloro-4'-(4-isopropylaminobutoxy)-3'-(5,5,8,8-tetramethyl-5,6,7,8-tetrahydronaphth-2-yl)biphenyl-4-carboxylic acid;
36. 2-Hydroxy-4'-(4-isopropylaminobutoxy)-3'-(5,5,8,8-tetramethyl-5,6,7,8-tetrahydronaphth-2-yl)biphenyl-4-carboxylic acid;
37. 6-[4-(4-Isopropylaminobutoxy)-3-(5,5,8,8-tetramethyl-5,6,7,8-tetrahydronaphth-2-yl)phenyl]nicotinic acid;
38. 5-[4-(4-Isopropylaminobutoxy)-3-(5,5,8,8-tetramethyl-5,6,7,8-tetrahydronaphth-2-yl)phenyl]pyridine-2-carboxylic acid;
39. 5-[4-(4-Isopropylaminobutoxy)-3-(5,5,8,8-tetramethyl-5,6,7,8-tetrahydronaphth-2-yl)phenyl]thiophene-2-carboxylic acid;
40. 5-[4-(4-Isopropylaminobutoxy)-3-(5,5,8,8-tetramethyl-5,6,7,8-tetrahydronaphth-2-yl)phenyl]furan-2-carboxylic acid;
41. 4-[4-(4-isopropylaminobutoxy)-3-(5,5,8,8-tetramethyl-5,6,7,8-tetrahydronaphth-2-yl)phenyl]furan-2-carboxylic acid;
42. 4-[4-(4-Isopropylaminobutoxy)-3-(5,5,8,8-tetramethyl-5,6,7,8-tetrahydronaphth-2-yl)phenyl]thiophene-2-carboxylic acid;
43. 5-[4-(4-Isopropylaminobutoxy)-3-(5,5,8,8-tetramethyl-5,6,7,8-tetrahydronaphth-2-yl)phenyl]thiophene-3-carboxylic acid;
44. 5-[4-(4-Isopropylaminobutoxy)-3-(5,5,8,8-tetramethyl-5,6,7,8-tetrahydronaphth-2-yl)phenyl]furan-3-carboxylic acid;
45. 4'-(4-Ethylaminobutoxy)-3-hydroxy-3'-(5,5,8,8-tetramethyl-5,6,7,8-tetrahydronaphth-2-yl)biphenyl-4-carboxylic acid;
46. 3-Hydroxy-4'-(4-propylaminobutoxy)-3'-(5,5,8,8-tetramethyl-5,6,7,8-tetrahydronaphth-2-yl)biphenyl-4-carboxylic acid;
47. 3-Hydroxy-4'-(3-propylaminopropoxy)-3'-(5,5,8,8-tetramethyl-5,6,7,8-tetrahydronaphth-2-yl)biphenyl-4-carboxylic acid;
48. 4'-(4-Piperidin-1-ylbutoxy)-3'-(5,5,8,8-tetramethyl-5,6,7,8-tetrahydronaphth-2-yl)biphenyl-4-carboxylic acid;
49. Ethyl 4'-(3-isopropylaminopropoxy)-3'-(5,5,8,8-tetramethyl-5,6,7,8-tetrahydronaphth-2-yl)biphenyl-4-carboxylate;
50. Ethyl 4'-(3-cyclopropylaminopropoxy)-3'-(5,5,8,8-tetramethyl-5,6,7,8-tetrahydronaphth-2-yl)biphenyl-4-carboxylate;
51. 4'-(3-Cyclopropylaminopropoxy)-3'-(5,5,8,8-tetramethyl-5,6,7,8-tetrahydronaphth-2-yl)biphenyl-4-carboxylic acid;
52. Ethyl 4'-(3-butylaminopropoxy)-3'-(5,5,8,8-tetramethyl-5,6,7,8-tetrahydronaphth-2-yl)biphenyl-4-carboxylate;
53. 4'-(3-Butylaminopropoxy)-3'-(5,5,8,8-tetramethyl-5,6,7,8-tetrahydronaphth-2-yl)biphenyl-4-carboxylic acid;
54. Ethyl 4'-(3-dimethylaminopropoxy)-3'-(5,5,8,8-tetramethyl-5,6,7,8-tetrahydronaphth-2-yl)biphenyl-4-carboxylate;
55. 4'-(3-Dimethylaminopropoxy)-3'-(5,5,8,8-tetramethyl-5,6,7,8-tetrahydronaphth-2-yl)biphenyl-4-carboxylic acid;
56. Ethyl 4'-(3-propylaminopropoxy)-3'-(5,5,8,8-tetramethyl-5,6,7,8-tetrahydronaphth-2-yl)biphenyl-4-carboxylate;
57. 4'-(3-Propylaminopropoxy)-3'-(5,5,8,8-tetramethyl-5,6,7,8-tetrahydronaphth-2-yl)biphenyl-4-carboxylic acid;
58. Ethyl 4'-(4-cyclopropylaminobutoxy)-3'-(5,5,8,8-tetramethyl-5,6,7,8-tetrahydronaphth-2-yl)biphenyl-4-carboxylate;
59. 4'-(4-Cyclopropylaminobutoxy)-3'-(5,5,8,8-tetramethyl-5,6,7,8-tetrahydronaphth-2-yl)biphenyl-4-carboxylic acid;
60. Ethyl 4'-(3-methylaminopropoxy)-3'-(5,5,8,8-tetramethyl-5,6,7,8-tetrahydronaphth-2-yl)biphenyl-4-carboxylate;
61. 4'-(3-Methylaminopropoxy)-3'-(5,5,8,8-tetramethyl-5,6,7,8-tetrahydronaphth-2-yl)biphenyl-4-carboxylic acid;
62. Ethyl 4'-(3-ethylaminopropoxy)-3'-(5,5,8,8-tetramethyl-5,6,7,8-tetrahydronaphth-2-yl)biphenyl-4-carboxylate;
63. 4'-(3-Ethylaminopropoxy)-3'-(5,5,8,8-tetramethyl-5,6,7,8-tetrahydronaphth-2-yl)biphenyl-4-carboxylic acid;
64. Ethyl 4'-(3-aminopropoxy)-3'-(5,5,8,8-tetramethyl-5,6,7,8-tetrahydronaphth-2-yl)biphenyl-4-carboxylate;
65. 4'-(3-Aminopropoxy)-3'-(5,5,8,8-tetramethyl-5,6,7,8-tetrahydronaphth-2-yl)biphenyl-4-carboxylic acid;
66. Ethyl 4'-(2-cyclopropylaminoethoxy)-3'-(5,5,8,8-tetramethyl-5,6,7,8-tetrahydronaphth-2-yl)biphenyl-4-carboxylate;
67. 4'-(2-Cyclopropylaminoethoxy)-3'-(5,5,8,8-tetramethyl-5,6,7,8-tetrahydronaphth-2-yl)biphenyl-4-carboxylic acid;
68. Ethyl 4'-(5-cyclopropylaminopentyloxy)-3'-(5,5,8,8-tetramethyl-5,6,7,8-tetrahydronaphth-2-yl)biphenyl-4-carboxylate;
69. 4'-(5-Cyclopropylaminopentyloxy)-3'-(5,5,8,8-tetramethyl-5,6,7,8-tetrahydronaphth-2-yl)biphenyl-4-carboxylic acid;
70. Ethyl 4'-(2-isopropylaminoethoxy)-3'-(5,5,8,8-tetramethyl-5,6,7,8-tetrahydronaphth-2-yl)biphenyl-4-carboxylate;
71. Ethyl 4'-(5-ethylaminopentyloxy)-3'-(5,5,8,8-tetramethyl-5,6,7,8-tetrahydronaphth-2-yl)biphenyl-4-carboxylate;
72. Ethyl 4'-(5-aminopentyloxy)-3'-(5,5,8,8-tetramethyl-5,6,7,8-tetrahydronaphth-2-yl)biphenyl-4-carboxylate;
73. 4'-(5-Aminopentyloxy)-3'-(5,5,8,8-tetramethyl-5,6,7,8-tetrahydronaphth-2-yl)biphenyl-4-carboxylic acid;
74. Ethyl 4'-(4-aminobutoxy)-3'-(5,5,8,8-tetramethyl-5,6,7,8-tetrahydronaphth-2-yl)biphenyl-4-carboxylate; and 75. 4'-(4-Aminobutoxy)-3'-(5,5,8,8-tetramethyl-5,6,7,8-tetrahydronaphth-2-yl)biphenyl-4-carboxylic acid.

17. A pharmaceutical composition useful for activating RAR receptors, comprising a thus effective amount of at least one ligand compound as defined by claim 1, formulated into a physiologically acceptable medium therefor.

18. The pharmaceutical composition as defined by claim 17, said at least one ligand compound comprising from 0.001% to 10% by weight thereof.

19. The pharmaceutical composition as defined by claim 17, said at least one ligand compound comprising from 0.01% to 1% by weight thereof.

20. A compound having a structure 4'-(4-Isopropylaminobutoxy)-3'-(5,5,8,8-tetramethyl-5,6,7,8-tetrahydronaphth-2-yl)biphenyl-4-carboxylic acid.

\* \* \* \* \*